(12) United States Patent
Swanson et al.

(10) Patent No.: US 8,906,645 B2
(45) Date of Patent: Dec. 9, 2014

(54) MICROBIAL DETECTION ARTICLE HAVING A WATER-ABSORBENT FILTER ASSEMBLY

(75) Inventors: Steven P. Swanson, Blaine, MN (US); Jesse D. Miller, Hudson, WI (US); Clinton P. Waller, Jr., White Bear Lake, MN (US); Neil Percy, St. Paul, MN (US); Jeffrey A. Lucas, Clinton, CT (US); Kannan Seshadri, Woodbury, MN (US); Jerald K. Rasmussen, Woodville, WI (US); Douglas E. Weiss, Overland Park, KS (US); James E. Aysta, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/809,214

(22) PCT Filed: Dec. 27, 2011

(86) PCT No.: PCT/US2011/067338
§ 371 (c)(1),
(2), (4) Date: Jan. 9, 2013

(87) PCT Pub. No.: WO2012/092242
PCT Pub. Date: Jul. 5, 2012

(65) Prior Publication Data
US 2013/0316393 A1 Nov. 28, 2013

Related U.S. Application Data

(60) Provisional application No. 61/428,029, filed on Dec. 29, 2010.

(51) Int. Cl.
*C12Q 1/04* (2006.01)
*C12Q 1/24* (2006.01)
*C12M 1/12* (2006.01)

(52) U.S. Cl.
CPC .. *C12Q 1/04* (2013.01); *C12Q 1/24* (2013.01); *C12M 25/02* (2013.01)
USPC .......................... 435/34; 435/287.1; 210/236

(58) Field of Classification Search
CPC ............ C12Q 1/04; C12Q 1/24; C12M 25/02
USPC ................................................. 435/34, 287.1
See application file for complete search history.

(56) References Cited

U.S. PATENT DOCUMENTS 3,849,241 A 11/1974 Butin
3,876,738 A 4/1975 Marinaccio
(Continued)

FOREIGN PATENT DOCUMENTS

EP 0 374 905 6/1990
GB 2 198 847 6/1988
(Continued)

OTHER PUBLICATIONS

Millipore, MF-Millipore Membrane, HAWG 04700, Accessed Feb. 5, 2014, online at: www.millipore.com/catalogue/item/hawg04700.*

(Continued)

*Primary Examiner* — Karen Cochrane Carlson
*Assistant Examiner* — Jennifer M. H. Tichy
(74) *Attorney, Agent, or Firm* — Jean A. Lown

(57) ABSTRACT

A microbial detection article and methods of using the same, the article comprising: a base member comprising a self-supporting water impervious substrate with first and second generally opposed major surfaces; a filter assembly defining a filter assembly aperture therein, and having a composite filter body mounted across the filter assembly aperture; wherein the composite filter body comprises: a microporous membrane, and a water-absorbent layer in fluid communication with the microporous membrane; and a cover sheet.

20 Claims, 7 Drawing Sheets

(56) References Cited

U.S. PATENT DOCUMENTS

| | | | |
|---|---|---|---|
| 4,118,531 | A | 10/1978 | Hauser |
| 4,157,418 | A | 6/1979 | Heilmann |
| 4,473,474 | A | 9/1984 | Ostreicher |
| 4,565,783 | A | 1/1986 | Hansen |
| 4,707,265 | A | 11/1987 | Barnes, Jr. |
| 4,767,426 | A | 8/1988 | Daly |
| 4,797,259 | A | 1/1989 | Matkovich |
| 4,936,934 | A | 6/1990 | Buehning |
| 5,006,247 | A | 4/1991 | Dennison |
| 5,089,413 | A | 2/1992 | Nelson |
| 5,147,801 | A | 9/1992 | Suzuki |
| 5,232,838 | A * | 8/1993 | Nelson et al. ............. 435/30 |
| 5,269,931 | A | 12/1993 | Hu |
| 5,348,861 | A | 9/1994 | Kulla |
| 5,364,766 | A | 11/1994 | Mach |
| 5,366,867 | A | 11/1994 | Kawakami |
| 5,443,963 | A | 8/1995 | Lund |
| 5,462,860 | A | 10/1995 | Mach |
| 5,494,823 | A | 2/1996 | Takemoto |
| 5,601,998 | A | 2/1997 | Mach |
| 5,635,367 | A | 6/1997 | Lund |
| 5,681,712 | A | 10/1997 | Nelson |
| 5,905,038 | A | 5/1999 | Parton |
| 6,056,529 | A | 5/2000 | Meyering |
| 6,230,776 | B1 | 5/2001 | Choi |
| 6,264,044 | B1 | 7/2001 | Meyering |
| 6,265,203 | B1 | 7/2001 | Ushiyama |
| 6,413,070 | B1 | 7/2002 | Meyering |
| 6,513,666 | B2 | 2/2003 | Meyering |
| 6,776,940 | B2 | 8/2004 | Meyering |
| 7,112,389 | B1 | 9/2006 | Arora |
| RE39,399 | E | 11/2006 | Allen |
| 7,170,739 | B1 | 1/2007 | Arora |
| 7,235,122 | B2 | 6/2007 | Bryner |
| 7,534,600 | B2 | 5/2009 | Gu |
| 8,328,023 | B2 * | 12/2012 | Weiss et al. ............. 210/503 |
| 2003/0211566 | A1 | 11/2003 | Gazenko |
| 2004/0101954 | A1 | 5/2004 | Graessle |
| 2004/0102903 | A1 | 5/2004 | Graessle |
| 2004/0116026 | A1 | 6/2004 | Kubose |
| 2007/0154651 | A1 | 7/2007 | Weiss |
| 2010/0075560 | A1 | 3/2010 | Seshadri |
| 2010/0155323 | A1 | 6/2010 | Weiss |
| 2010/0261801 | A1 | 10/2010 | Weiss |
| 2011/0171683 | A1 | 7/2011 | Mach |
| 2011/0244511 | A1 | 10/2011 | Mach |
| 2012/0003686 | A1 * | 1/2012 | Kshirsagar et al. ............. 435/34 |

FOREIGN PATENT DOCUMENTS

| | | |
|---|---|---|
| JP | 8-26547 | 8/1996 |
| JP | 9-206062 | 8/1997 |
| JP | 2001-245693 | 9/2001 |
| JP | 2001-321196 | 11/2001 |
| JP | 2003-189896 | 7/2003 |
| WO | WO 92/04971 | 4/1992 |
| WO | WO 96/37600 | 11/1996 |
| WO | WO 2005/024047 | 3/2005 |
| WO | WO 2009/082667 | 7/2009 |
| WO | WO 2010/077619 | 7/2010 |
| WO | WO 2010/147918 | 12/2010 |
| WO | WO 2010/151447 | 12/2010 |
| WO | WO 2012/012172 | 1/2012 |
| WO | WO 2012/024128 | 2/2012 |

OTHER PUBLICATIONS

Davies, C. N., "The Separation of Airborne Dust and Particles," Institution of Mechanical Engineers, London, Proceedings 1B, (1952).

Sadler et al., *J. Am Chem. Soc.* 78:1251-1255, (1956).

Wente et al., Manufacture of Superfine Organic Fibers, (*Naval Research Laboratories Report* No. 4364, (1954).

Wente, Superfine Thermoplastic Fibers, 48 *Indus. Eng. Chem.* 1342 (1956).

Written Opinion of the ISA for International Application No. PCT/US2011/042348, 7 pgs, 2012.

International Search Report for PCT/US2011/042348, 4 pages, 2012.

* cited by examiner

MICROBIAL DETECTION ARTICLE HAVING A WATER-ABSORBENT FILTER ASSEMBLY

BACKGROUND

When surfaces become contaminated with bacteria, fungi, yeasts, viruses, or other microorganisms, or "microbes," sickness (morbidity) and, sometimes, death (mortality) may result. This is particularly true when surfaces in food processing plants and healthcare facilitates (e.g., hospitals) become contaminated with microorganisms.

In food processing plants, surfaces (e.g., solid surfaces, equipment surfaces, protective clothing, etc.) may become contaminated. Such contamination may be caused by or transferred to meat or other foods. In healthcare facilities, microbes may be released onto surfaces (e.g., solid surfaces, equipment surfaces, clothing, etc.) from infected individuals. Once a surface becomes contaminated with microbes, contact with the contaminated surface may easily and readily transfer microbes to other locations, such as another surface, an individual, equipment, or food.

As is well known, microbial contamination and transfer in certain environments may pose significant health risks. For example, the food that leaves a contaminated food processing plant will subsequently be eaten, and may cause sickness and, possibly, death. Microorganisms such as *Listeria monocytogenes*, *Salmonella enteriditis*, and *Escherichia coli* O157:H7 are of particular concern.

Microbial contamination is of concern in healthcare facilities since some of the patients of such facilities often suffer from infections by pathogenic microbes and, thus, bring the pathogenic microbes into such facilities. Further, many of those who are present in such facilities (e.g., patients) are sick and may be immunologically compromised. These individuals are, thus, at increased risk of becoming sick from infection by the contaminating microbes.

SUMMARY

There is a need for a microbial detection article that simplifies the sample preparation and test device conditioning required for detecting the presence of microorganisms in an aqueous sample.

In one aspect, the current disclosure provides a microbial detection article that includes: a base member, a filter assembly, and a cover sheet. The base member comprises a self-supporting water impervious substrate with first and second generally opposed major surfaces. The filter assembly defines a filter assembly aperture therein, and has a composite filter body mounted across the filter assembly aperture. The composite filter body comprises a microporous membrane, and a water-absorbent layer in fluid communication with the microporous membrane. The filter assembly is positioned between the cover sheet and the base member, and the water-absorbent layer is positioned between the microporous membrane and the base member.

In another aspect, the current disclosure provides a method of testing for the presence of a microorganism in an aqueous sample. The method includes providing a microbial detection article of the current disclosure, providing an aqueous sample, and passing the aqueous sample firstly through the microporous membrane and secondly through the water-absorbent layer. The water absorbent layer retains an aliquot of water from the aqueous sample. The microbial detection article is incubated for an incubation period, and at least a portion of the aliquot of water contacts the microporous membrane throughout the incubation period. An observation is made for the presence or absence of microbial growth.

"Hydrogel", as used herein, refers to a water-containing gel, having polymer chains that are hydrophilic and will absorb water, yet are insoluble in water. The term hydrogel is used regardless of the state of hydration.

"Microporous", as used herein, refers to a water-permeable material having pores within a nominal range of 0.05 micrometer to 1.2 micrometer.

"Self-supporting", as used herein, refers to a material that is able to support its own weight.

"Target microorganism", as used herein, refers to a particular microorganism (i.e., a species of microorganism) or a particular group of microorganisms (e.g., a particular genus of microorganisms, coliform bacteria, antibiotic-resistant bacteria) to be detected.

"Water-absorbent", as used herein, refers to material having a capacity to absorb water at a level of at least 20 weight percent relative to a weight of the material.

"Water-absorption capacity", as used herein, refers to a weight of water absorbed relative to a weight of water-absorbent material.

"Water activity" or "$A_W$", as used herein, refers to the availability of water and represents the energy status of the water in a system. It is defined as the vapor pressure of water above a sample divided by that of pure water at the same temperature. Pure distilled water has a water activity of exactly one. In general, an $A_W$ value of at least 0.91 is useful for supporting microbial growth.

"Water-soluble", as use herein, refers to the temperature of water below which a gelling agent can be reconstituted by hydration. In its most convenient usage the gelling agent may be reconstituted at about 20° C., while in some instances a temperature of up to about 90° C. may be acceptable, as long as the temperature does not adversely affect viability of target microorganisms.

Figure 1A:
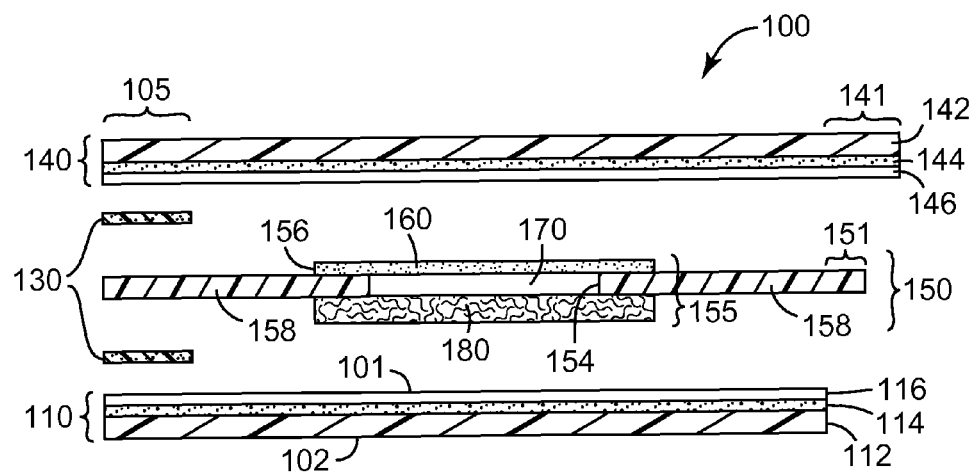
FIGS. 1A and 1B are an exploded side view and a top view, respectively, of an embodiment of a microbial detection article according to the current description.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the disclosure. In particular the dimensions of the various components are depicted in illustrative terms only, and no relationship between the dimensions of the various components should be inferred from the drawings, unless so indicated. Although terms such as "top", "bottom", "upper", "lower", "under", "over", "front", "back", "outward", "inward", "up" and "down", and "first" and "second" may be used in this disclosure, it should be understood that those terms are used in their relative sense only unless otherwise noted. In particular, in some embodiments certain components may be present in interchangeable and/or identical multiples (e.g., pairs). For these components, the designation of "first" and "second" may apply to the order of use, as noted herein (with it being irrelevant as to which one of the components is selected to be used first).

DETAILED DESCRIPTION

Unless otherwise defined, all technical and scientific terms used herein have the same meaning as commonly understood by one of ordinary skill in the art to which the current disclosure belongs. Methods and materials similar or equivalent to those described herein can be used in the practice of the embodiments of the present disclosure, and exemplified suitable methods and materials are described below. For example, methods may be described that comprise more than two steps. In such methods, not all steps may be required to achieve a defined goal and the present disclosure envisions the use of isolated steps to achieve these discrete goals. In addition, the materials, methods, and examples are illustrative only and not intended to be limiting.

The articles and methods of the present disclosure may be used for a variety of applications where it is desirable to detect the presence or absence of microorganisms in a sample including, but not limited to, food samples (e.g., raw materials, in-process food materials, finished products), surfaces (e.g., environmental surfaces, food processing surfaces, equipment), water (e.g., surface water, process water), and beverages (e.g., raw milk, pasteurized milk, juice). The samples may consist of solid, semi-solid, gelatinous, or liquid material, alone or in various combinations. The devices of the current description, as well as the described methods, may be used to determine, qualitatively or quantitatively, the presence of one or more microorganisms of interest.

An exemplary clinical analyte of interest to detect is *Staphylococcus aureus* ("*S. aureus*"). This is a pathogen causing a wide spectrum of infections including: superficial lesions such as small skin abscesses and wound infections; systemic and life threatening conditions such as endocarditis, pneumonia and septicemia; as well as toxinoses such as food poisoning and toxic shock syndrome. Some strains (e.g., Methicillin-Resistant *S. aureus* or MRSA) are resistant to all but a few select antibiotics.

Exemplary analytes of interest to detect in food processing areas are members of the genus *Listeria*. *Listeria* are classified as gram-positive, rod-shaped bacteria and include the species *Listeria monocytogenes*, *L. innocua*, *L. welshimeri*, *L. seeligeri*, *L. ivanovii*, and *L. grayi*. Among these, *L. monocytogenes* is responsible for the majority of human listeriosis cases and immunocompromised, pregnant women, elderly, and newborns have increased susceptibility to infection. The most common symptoms of listeriosis are septicemia, meningitis, and miscarriages.

Other microorganisms of particular interest for analytical purposes include prokaryotic and eukaryotic organisms, particularly Gram positive bacteria, Gram negative bacteria, fungi, mycoplasma, and yeast. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Vibrio* spp., *Clostridium* spp., *Corynebacteria* spp. as well as, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis*, *Streptococcus pneumoniae*, *S. agalactiae*, *S. pyogenes*, *Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis*, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Vibrio cholera*, *V. parahemolyticus*, *Salmonella cholerasuis*, *S. typhi*, *S. typhimurium*, *Candida albicans*, *C. glabrata*, *C. krusei*, *Enterobacter sakazakii*, *Escherichia coli* O157, ESBL-containing microorganisms, and multiple drug resistant Gram negative rods (MDR).

FIG. 1A shows an exploded side view of one embodiment of an article 100 according to the present disclosure, useful for detecting microorganisms. The article comprises: a base member 110 with first and second generally opposed major surfaces 101 and 102; a cover sheet 140; and a filter assembly 150. Filter assembly 150 has a filter assembly aperture 154 defined therein, and a composite filter body 155 mounted across filter assembly aperture 154, wherein the composite filter body includes a microporous membrane 160 and a water-absorbent layer 180. The water-absorbent layer 180 is in fluid communication with the microporous membrane 160. The filter assembly 150 is positioned between the cover sheet 140 and the base member 110, wherein the water-absorbent layer 180 is positioned between the microporous membrane 160 and the base member 110.

Figure 1B:
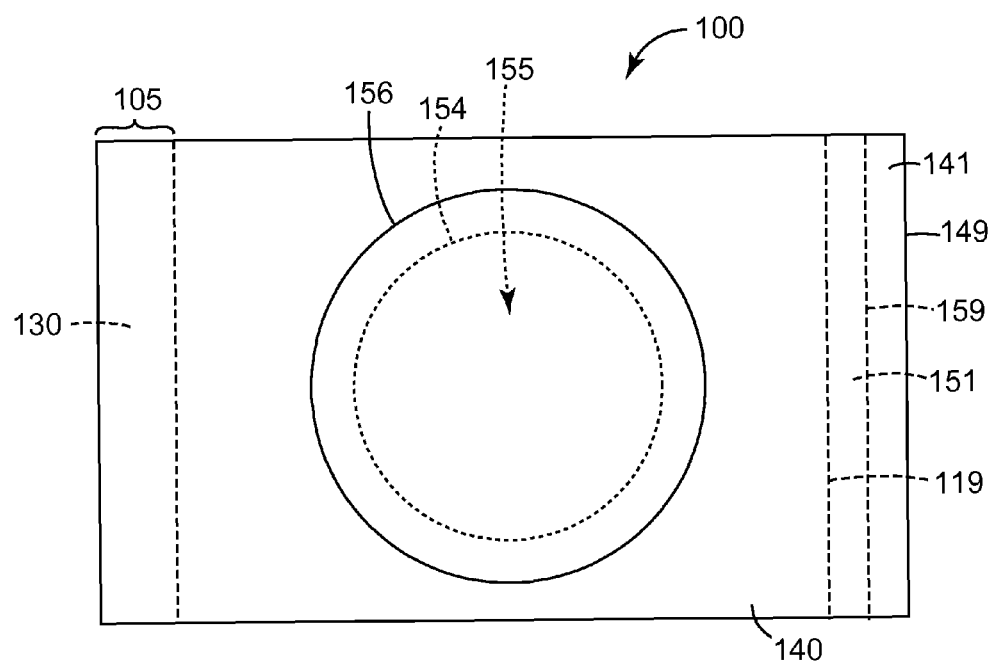

Referring now to FIGS. 1A and 1B, in some embodiments of article 100 the filter assembly 150 has an attachment portion 105 that is coupled to the base member 110. In the illustrated embodiment, the filter assembly 150 is coupled to the base member 110 at attachment portion 105 via a strip of double-sided adhesive tape 130, although a person of ordinary skill in the art will recognize that other coupling techniques (e.g., adhesives, heat-bonding, ultrasonic welding, stitching, or stapling) may be suitable. In some embodiments, the filter assembly 150 can be dimensioned to be at least coextensive with the dimensions of the base member 110. Coupling the filter assembly 150 to the base member 110, as described above, advantageously can keep the filter assembly 150 properly positioned within article 100.

The cover sheet 140 preferably is coupled (either directly or indirectly) to the base member 110. In the illustrated embodiment, the cover sheet 140 is coupled to the filter assembly 150 via a strip of double-sided adhesive tape 130. It is recognized that other coupling means (e.g., adhesives, heat-bonding, ultrasonic welding, stitching, or stapling) may be suitable to attach the cover sheet 140 to the filter assembly 150. It is also recognized that the cover sheet 140 may be coupled directly to the base member 110, provided that the filter assembly 150 is disposed between the base member 110 and the cover sheet 140.

In some further embodiments, the filter assembly 150 may comprise a tab region 151. The tab region 151 may extend beyond a peripheral boundary 119 of the base member 110. Similarly, the tab region 151 may extend beyond a peripheral boundary 149 of the cover sheet 140.

In some other embodiments, the cover sheet 140 may comprise a tab region 141. The tab region 141 may extend beyond the peripheral boundary 119 of the base member 110. Similarly, the tab region 141 may extend beyond the peripheral boundary 159 of the filter assembly 150. It will be understood that any suitable combination of the tab regions may be provided in order to facilitate peeling back the cover sheet 140 and the base member 110 and exposing the filter assembly 150 for a filtering operation.

Figure 2:
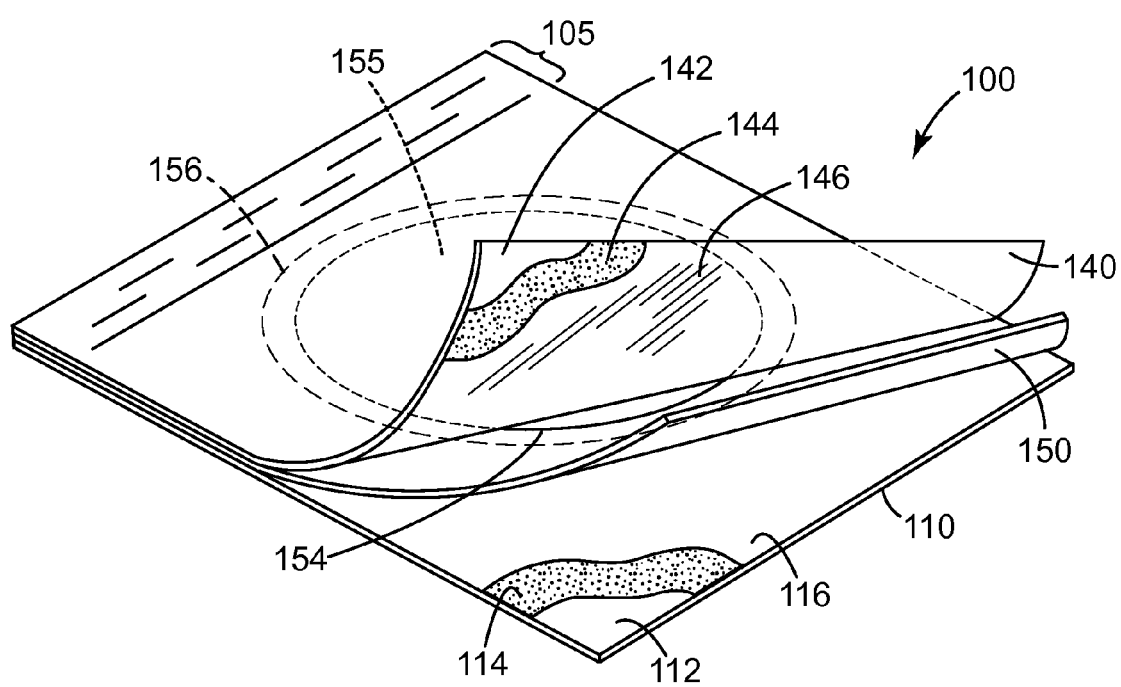
FIG. 2 is a perspective view of an embodiment of a microbial detection article of the current description.

FIG. 2 shows a perspective view of an embodiment of a microbial detection article of the current description. Cover sheet 140 is preferably flexible, and is typically selected to allow the cover sheet 140 to be manually peeled back from filter assembly 150, with minimal difficulty. In some embodiments, filter assembly 150 may also be flexible. Base member 110 may also be flexible, although typically base member 110 is selected to be self-supporting and is less flexible than cover sheet 140.

Figure 3A:
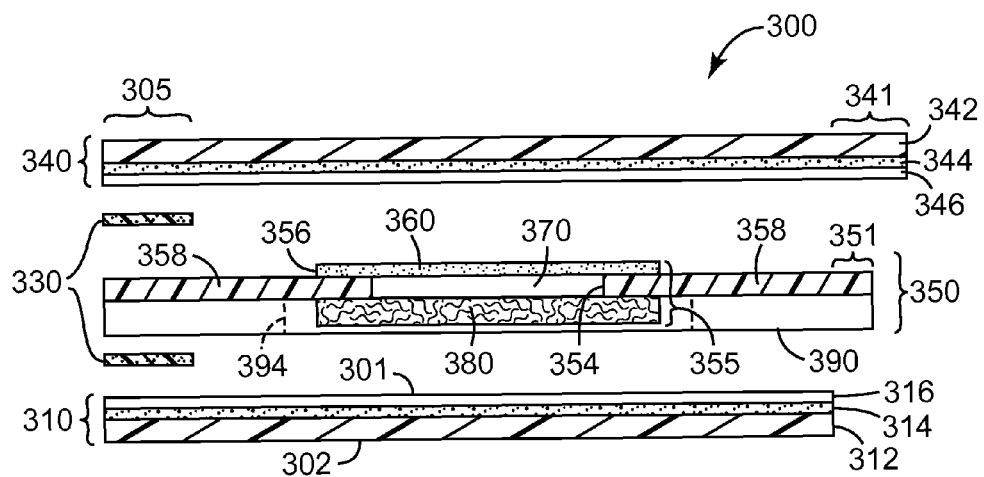
FIGS. 3A and 3B are an exploded side view and a top view, respectively, of an embodiment of a microbial detection article according to the current description, including a spacer layer.
Figure 3B:
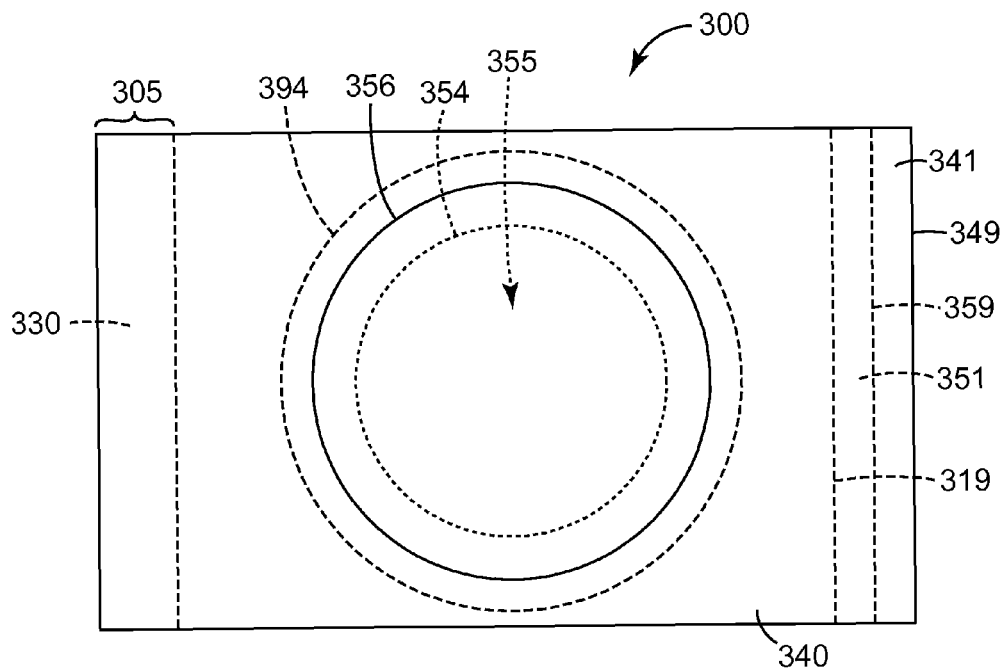

FIGS. 3A and 3B show an embodiment of an article 300 that in general has parts and part numbers that correspond to parts and part numbers in the article 100 (see FIGS. 1A and 1B), differing in that filter assembly 350 further comprises a spacer layer 390 defining a spacer layer aperture 394 therein, wherein the spacer layer 390 is mounted on a major face of the filter assembly 350 facing a first major surface 301 of base member 310, and wherein the spacer layer aperture 394 is in fluid communication with filter assembly aperture 354. When article 100 is mentioned in the current description, it will be understood that article 100 may comprise a spacer layer as described for article 300.

Referring again to FIG. 2, in some embodiments, the base member 110 includes a first substrate 112, an optional first adhesive layer 114 adhered to the first substrate 112, and an optional first dry coating 116. The first substrate 112 is "self-supporting" (i.e., is able to support its own weight) and "water impervious" (i.e., does not absorb water at a level of more than 10 weight percent). Some examples of suitable materials for the first substrate 112 include polyester, polypropylene, or polystyrene films. Other examples of suitable materials for the first substrate 112 include paper or cardboard materials that comprise a waterproof (e.g., polymeric) coating. The first substrate 112 may be transparent, translucent, or opaque, depending on whether one wishes to view bacterial colonies through the first substrate 112. To facilitate the counting of bacterial colonies, the first substrate 112 may have a square grid pattern printed thereon as described, for example, in U.S. Pat. No. 4,565,783 (Hansen et al.). The materials used to construct the first substrate 112 should be inert to microorganisms and, preferably, should be compatible with a sterilization process (e.g., ethylene oxide sterilization).

It should be understood that while FIG. 2 shows the base member 110 as including the optional first dry coating 116, in some typical embodiments the base member may not include a cold-water soluble gelling agent or nutrients, and instead will include a cold-water soluble gelling agent and nutrients in the cover sheet 140. In some more typical embodiments, the cover sheet 140 includes a second substrate 142, an optional second adhesive layer 144, and an optional second dry coating 146. In some embodiments, the optional second dry coating 146 comprises a detection reagent to detect a microorganism. In some embodiments, the optional second dry coating 146 comprises a nutrient medium.

The second substrate 142 preferably is transparent or translucent, to permit viewing or imaging of bacterial colonies through the second substrate 142, and does not absorb water at a level of more than about 20 weight percent. Non-limiting examples of suitable materials for the second substrate 142 include polyester, polypropylene, or polystyrene films. Preferably, the cover sheet 140 is flexible. The materials used to construct the second substrate 142 should be inert to microorganisms and, preferably, should be compatible with a sterilization process (e.g., ethylene oxide sterilization).

In some embodiments of the article 100, the base member 110 may include the optional first dry coating 116 adhered to the first substrate 112 by the optional first adhesive layer 114. In some typical embodiments of the article 100, the cover sheet 140 includes the optional second dry coating 146 adhered to the second substrate 142 by the optional second adhesive layer 144. In typical embodiments, an optional dry coating is included in one of either the cover sheet or the base member, and most typically an optional dry coating is included in only the cover sheet.

When included in the article 100, the optional first adhesive layer 114 and/or the optional second adhesive layer 144 comprises an adhesive material that is typically water-insoluble, should be non-inhibitory to the growth of microorganisms, and should be capable of withstanding the sterilization process, if a sterilization process is used. Preferably, the adhesive material is sufficiently transparent when wet to enable the viewing of bacterial colonies through the respective substrate layer to which it is adhered. In some embodiments, the adhesive material may comprise a pressure-sensitive adhesive, for example, a pressure sensitive iso-octyl acrylate/acrylic acid copolymer adhesive. A suitable pressure sensitive adhesive may contain iso-octyl acrylate in a range from 90 weight percent to 99 weight percent and acrylic acid in a range from 1 weight percent to 10 weight percent of acrylic acid, and a particularly suitable pressure sensitive adhesive has 96 weight percent iso-octyl acrylate and 4 weight percent acrylic acid.

When included in the article 100, the optional first dry coating 116 and/or the optional second dry coating 146, when included, comprises a water-soluble gelling agent (e.g., guar gum, xanthan gum, locust bean gum), as described, for example, in U.S. Pat. No. 4,565,783 (Hansen et al.). Optionally, the dry coating 116 and/or 146 may further comprise a nutrient medium, a selective agent, a detection reagent, or any combination of two or more of the foregoing. The nutrient medium, selective agent, and/or detection reagent should not interfere with the gelling agent and generally will be chosen based upon the microorganisms to be detected. Non-limiting examples of suitable nutrients, selective agents and detection reagents to detect microorganisms can be found, for example, in U.S. Pat. No. 4,565,783 (Hansen et al.); U.S. Pat. No. 5,089,413 (Nelson et al.); U.S. Pat. No. 5,364,766 (Mach et al.); U.S. Pat. No. 5,443,963 (Lund); U.S. Pat. No. 5,462,860 (Mach); U.S. Pat. No. 5,601,998 (Mach et al.); U.S. Pat. No. 5,635,367 (Lund); and U.S. Pat. No. 5,681,712 (Nelson). "Standard Methods Nutrients", as used herein, refers to the nutrient mixture described in Standard Methods for the Examination of Dairy Products, 14th Edition, American Public Health Association, Washington, D.C. It consists of 5 parts (by weight) peptone, 2.5 parts yeast extract and 1 part dextrose. The amounts of nutrient medium, selective agent and/or detection reagent are prepared such that, when contacted with a predetermined amount of liquid sample, they facilitate the growth and/or detection of a microorganism.

In some embodiments, the first dry coating 116 and/or the second dry coating 146 (e.g., a dry powder gelling agent; optionally with a dry powdered nutrient, selective agent and/or detection reagent) may be coupled to the respective first substrate 112 and/or second substrate 142 via the adhesive material, as described, for example, in U.S. Pat. No. 4,565,783 (Hansen et al.), or by coating a liquid mixture comprising a gelling agent (optionally including a dry powdered nutrient, selective agent and/or detection reagent) onto the respective substrate or adhesive layer and subsequently drying the mixture, as described, for example, in U.S. Pat. No. 4,565,783 (Hansen et al.).

In some embodiments, the first substrate 112 may comprise a first dry coating 116 that covers an entire major surface of the first substrate 112. In some embodiments, the first substrate 112 may comprise a first dry coating 116 that covers only a portion of a major surface of the first substrate 112.

In some embodiments, the second substrate 142 may comprise a second dry coating 146 that covers an entire major surface of the second substrate 142. In some embodiments, the second substrate 142 may comprise a second dry coating 146 that covers only a portion of a major surface of the second substrate 142.

In typical embodiments, the cover sheet 140 of the microbial detection article comprises the second dry coating 146 that includes the water-soluble gelling agent described supra. In some typical embodiments, the cover sheet 140 of the microbial detection article comprises the second dry coating 146 that includes the nutrient medium described supra. In some typical embodiments, the cover sheet 140 of the microbial detection article comprises the second dry coating 146 that includes the detection reagent described infra. In some typical embodiments, the cover sheet 140 of the microbial detection article comprises the second dry coating 146 that includes the water-soluble gelling agent, the nutrient medium, and the detection reagent, or any combination of these. The inclusion of the water-soluble gelling agent and the nutrient medium in the second dry coating 146 of the cover sheet 140 is useful for providing for growth of microorganism (if present on the microporous membrane 160), and the inclusion of the detection reagent in the second dry coating 146 of the cover sheet 140 is useful for observing an indication of the presence or absence of microbial growth.

The detection reagent may be detected visually and/or by using an automated detector. The automated detector may comprise an imaging system. The detection reagent may be chromogenic, fluorogenic, or luminogenic. In any embodiment, the detection reagent, when contacted with a predetermined amount of liquid sample reaches a concentration sufficient to detect a target microorganism. Advantageously, the amount of the detection reagent in the first dry coating 116 (or second dry coating 146) can be sufficiently high to rapidly detect the presence of a target microorganism even though the high concentration of detection reagent in the liquid sample also inhibits the growth of the target microorganism. In some embodiments, the amount of detection reagent in the first dry coating 116 (or second dry coating 146) is sufficient to detect a target microorganism even though it inhibits the growth of the target microorganism. A relatively higher amount of detection reagent in the first dry coating 116 (or second dry coating 146) permits more rapid detection of the target microorganisms than a relatively lower amount of detection reagent even though the relatively higher amount may inhibit growth of the microorganisms.

The detection reagent can be a nonspecific indicator of the type of microorganism present or it can be a specific indicator of the type of microorganism present. Non-limiting examples of nonspecific detection reagents include pH indicators (e.g., azobenzene pH indicators (e.g., methyl red), sulfonphthalein pH indicators (e.g., bromcresol purple, chlorophenol red, bromthymol blue, bromcresol blue), anthroquinone pH indicators (e.g., alizarin red s monohydrate 3,4-dihydroxy-9,10-dioxo-2-anthracensulfonic acid, sodium salt)), and redox indicators (e.g., triphenyltetrazolium chloride (TTC), 3-[4,5-dimethylthiazol-2-yl]-2,5-diphenyltetrazolium bromide (MTT), 2,3-bis[2-methoxy-4-nitro-5-sulfopheny]-2H-tetrazolium-5-carboxyanilide inner salt (XTT), Nitro Blue Tetrazolium).

The detection reagent can be a specific indicator of the type of microorganism present. Specific detection reagents include, for example, substrates for enzymes (e.g., glycosidases, proteases, aminopeptidases, and phosphatases, esterases) that are associated with certain microorganisms or groups of microorganisms.

The detection reagent may be capable of forming a colored precipitate. A variety of dyes are known that could be incorporated into the methods and devices of the present disclosure, including indolyl-containing dyes, for example 5-bromo-4-chloroindolyl phosphate or disodium salts of that compound, 5-bromo-4-chloroindolyl pyranoside or disodium salts of that compound, 5-bromo-4-chloro-3 indolyl-β-D-glucuronic acid, 5-bromo-4-chloro-3-indoxyl-β-D-galactoside, 5-bromo-4-chloro-3-indolyl-β-D-glucopyranoside, 6-chloro-3-indolylphosphate, and 5-bromo-6-chloro-3-indolylphosphate.

Preferably, the colored precipitate is blue. Substrates that create a blue colored precipitate include, for example, 5-bromo-4-chloro-3-indoxyl-N-acetyl-β-D-galactosaminide, 5-bromo-4-chloro-3-indoxyl-N-acetyl-β-D-glucosaminide, 5-bromo-4-chloro-3-indoxyl-β-D-cellobioside, 5-bromo-4-chloro-3-β-D-fucopyranoside, 5-bromo-4-chloro-3-indoxyl-α-D-galactopyranoside, 5-bromo-4-chloro-3-indoxyl-β-galactopyranoside, 5-bromo-4-chloro-3-indoxyl-α-D-glucopyranoside, 5-bromo-4-chloro-3-indoxyl-β-D-glucopyranoside, 5-bromo-4-chloro-3-indoxyl-β-D-glucuronic acid, cyclohexylammonium salt, 5-bromo-4-chloro-3-indoxyl-β-D-glucuronic acid, sodium salt, and 5-bromo-4-chloro-3-indoxyl-β-D-xylopyranoside.

The dyes can serve as substrates for particular enzymes present within certain types of bacteria. Blue-precipitate producing dyes that are substrates for esterases include, for example, 5-bromo-4-chloro-3-indoxyl butyrate, 5-bromo-4-chloro-3-indoxyl caprylate, and 5-bromo-4-chloro-3-indoxyl palmitate. Substrates for phosphatases include, but are not limited to, 5-bromo-4-chloro-3-indoxyl phosphate di(2-amino-2-methyl-1,3-propanediol) salt, 5-bromo-4-chloro-3-indoxyl phosphate disodium salt, 5-bromo-4-chloro-3-indoxyl phosphate and p-toluidine salt, 5-bromo-4-chloro-3-indoxyl phosphate and the potassium salt.

Chromogenic dyes that are substrates for glycosidases include, for example, 3-indoxyl-β-D-galactopyranoside, 3-indoxyl-β-D-glucopyranoside, 3-indoxyl-β-D-glucuronic acid cyclohexylammonium salt, and 3-indoxyl-β-D-glucuronic acid sodium salt. Other chromogenic substrates for phophatases include, for example, 3-indoxyl phosphate di(2-amino-2-methyl-1,3-propanediol) salt, 3-indoxyl phosphate disodium salt, and 3-indoxyl phosphate p-toluidine salt. Substrates for sulfatases include, for example, 3-indoxyl sulfate potassium salt.

Precipitable dyes that produce a magenta color for glycosidases, esterases, phosphatases and sulfatases include, for example, 5-bromo-6-chloro-3-indoxyl-N-acetyl-β-D-glucosaminide, 5-bromo-6-chloro-3-indoxyl-β-D-galactopyranoside, 5-bromo-6-chloro-3-indoxyl-β-D-galactopyranoside, 5-bromo-6-chloro-3-indoxyl-β-D-glucopyranoside, 5-bromo-6-chloro-3-indoxyl-β-glucuronic acid, cyclohexylammonium salt as substrates for glycosidases; 5-bromo-6-chloro-3-indoxyl butyrate, 5-bromo-6-chloro-3-indoxyl caprylate, and 5-bromo-6-chloro-3-indoxyl palmitate serve as substrates for esterases; 5-bromo-6-chloro-3-indoxyl phosphate, p-toluidine salt for phosphatases and 5-bromo-6-chloro-3-indoxyl sulfate, potassium salt serve as substrates for sulfatases.

Precipitable dyes that produce a salmon color for glycosidases, esterases and phosphatases include, for example, 6-chloro-3-indoxyl-β-galactopyranoside, 6-chloro-3-indoxyl-β-D-glucopyranoside, and 6-chloro-3-indoxyl-β-D-glucuronic acid, cyclohexylammonium salt for glycosidases; 6-chloro-3-indoxyl butyrate, 6-chloro-3-indoxyl caprylate, and 6-chloro-3-indoxyl palmitate for esterases; and, 6-chloro-3-indoxyl phosphate, p-toluidine salt for phosphatases.

Chromogenic substrates that produce a purple color include 5-iodo-3-indoxyl-β-D-galactopyranoside and chromogenic substrates that produce a green color include N-methyl-indoxyl-β-D-galactopyranoside.

Other precipitable dyes include 4,6-dichloro-N-acetylindol-3-ol, 6-chloroindolyl-β-D-galactoside pentaacetate, 6-chloroindolyl-β-D-galactoside, 6-chloroindoxy-1,3-diacetate, 5-chloro-2-carboxyphenylglycine sodium salt, 4-chloroanthranilic acid, methyl[6-chloro-N-acetylindol-3-yl-(2,3,4-tri-O-acetyl-β-D-glucopyran oside)]uronate, 6-chloroindolyl-β-D-glucopyranoside uronate monocyclohexylammonium salt, chloroindigos (including those chloroindigos reported by Sadler et al., J. Am. Chem. Soc. 78:1251-1255, 1956), as well as 4,6-dichloroindolyl-β-D-glucuronide, 6,7-dichloroindolyl-β-D-glucuronide, 6,7-dichloroindolyl-β-D-glucuronide, 4,6,7-trichloroindolyl-β-D-glucuronide, 4,6-dichloroindolyl-β-D-galactoside, 6,7-dichloroindolyl-β-D-galactoside, and 4,6,7-trichloroindolyl-β-D-galactoside.

Suitable detection reagents further include non-precipitating indicator dyes (i.e., water-soluble dyes that are capable of diffusing in a hydrogel). Non-precipitating indicator dyes include pH indicators (e.g., azobenzene pH indicators, sulfonphthalein pH indicators, and anthroquinone pH indicators, as described herein. Non-precipitating indicator dyes also include chromogenic enzyme substrates that react with an enzyme to release a water-soluble dye (e.g., p-nitrophenyl phosphate or p-nitrophenyl-β-D-glucoside, which each can be hydrolyzed to p-nitrophenol), and fluorogenic enzyme substrates, which can react with an enzyme to release a water-soluble fluorescent dye (e.g., 4-methylumbelliferyl phosphate or 4-methylumbelliferyl-β-D-glucoside, which each can be hydrolyzed to 4-methylumbelliferone).

In the embodiment of article 100 shown in FIGS. 1A and 1B, the filter assembly 150 is shown to have a filter support layer 158 having the filter assembly aperture 154 defined therein, and the composite filter body 155 mounted across the filter assembly aperture. The filter support layer 158 is configured to composite filter body 155. The filter support layer 158 preferably is self-supporting and does not absorb water, or absorbs water at a level of less than 10 weight percent. Non-limiting examples of suitable materials for the filter support layer 158 include polyester, polypropylene, or polystyrene films. Other suitable materials include paper or cardboard materials that comprise a waterproof (e.g., polymeric) coating. The filter support layer 158 may be transparent, translucent, or opaque. Optionally, the filter support layer 158 may comprise a tab region 151 that extends beyond a peripheral boundary of the base member 110 and/or the cover sheet 140.

The filter support layer 158 further comprises a filter assembly aperture 154 defined therein that permits fluid communication from the base member 110 through the filter assembly 150 to the cover sheet 140. The filter assembly aperture 154 can be any shape, such as a circle, a square, a rectangle, a hexagon, an octagon, an oval, or an irregular shape, for example.

The composite filter body 155 includes the microporous membrane 160 and the water-absorbent layer 180, and in FIG. 1A the microporous membrane 160 and water-absorbent layer 180 are shown as being mounted on opposed major faces of filter support layer 158, and defining a gap 170 therebetween. The water-absorbent layer 180 is in fluid communication with the microporous membrane 160. It will be understood that in some embodiments, at least a portion of the microporous membrane 160 may contact at least a portion of the water-absorbent layer 180, and that in some embodiments the gap 170 may not be continuous across the filter assembly aperture 154, and that in some embodiments, the microporous membrane 160 and the water-absorbent layer may contact each other throughout an area defined by the filter assembly aperture 154.

The microporous membrane 160 should be positioned such that, during use, at least a portion of the microporous membrane 160 overlays the filter assembly aperture 154. Preferably, during use, the microporous membrane 160 is positioned such that the microporous membrane 160 overlays the filter assembly aperture 154. In some embodiments, the area of the microporous membrane 160 is larger than the area of the filter assembly aperture 154 and the microporous membrane 160 extends beyond the perimeter of the filter assembly aperture 154.

In the embodiment of article 300 shown in FIGS. 3A and 3B, filter assembly 350 further comprises a spacer layer 390 defining a spacer layer aperture 394 therein, wherein the spacer layer 390 is mounted on a major face of filter support layer 358 facing a first major surface 301 of base member 310, and wherein the spacer layer aperture 394 is in fluid communication with filter assembly aperture 354. The spacer layer 390 should be constructed from a water-insoluble material. The walls of the aperture spacer layer, together with filter support layer 358, form a liquid sample well of predetermined size and shape to confine a volume of liquid sample (e.g., an aqueous sample) within the article 300. The spacer layer 390 should be thick enough and the spacer layer aperture 394 large enough to form a well of the desired volume (e.g., 1 milliliter, 2 milliliters, 3 milliliters, 5 milliliters, or more). Closed cell polyethylene foam or polystyrene foam are suitable materials for the spacer layer 390, but any material which is hydrophobic (non-wetting), inert to microorganisms, and, preferably, capable of withstanding a sterilization process may be used. The spacer layer 390 can be coupled to the filter support layer 358, for example, by an adhesive, as described for example in U.S. Pat. No. 4,565,783 (Hansen et al.).

Figure 4A:
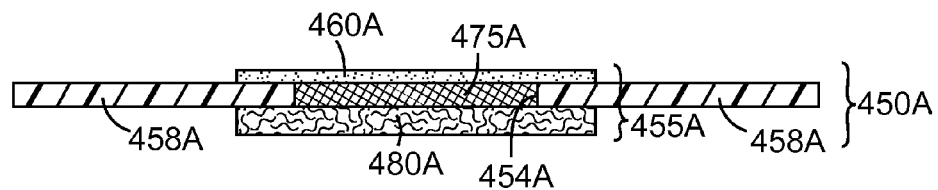
FIGS. 4A-4D are side views of alternate embodiments of a filter assembly for a detection article of the current description.

FIGS. 4A-4D show several alternative embodiments for positioning the microporous membranes 460A-D and the water-absorbent layers 480A-D across the filter assembly apertures 454A-D. FIG. 4A shows a filter assembly 450A having features essentially the same as the filter assembly 150 in FIGS. 1A and 1B, but including an optional scrim 475A positioned within composite filter body 455A, between microporous membrane 460A and water-absorbent layer 480A. The optional scrim 475A may be useful to provide reinforcement for the composite filter body 455A, while maintaining fluid communication of the water-absorbent layer 480A with the microporous membrane 460A. Scrim materials are described along with a more detailed description of the water-absorbent layer, below.

Figure 4B:
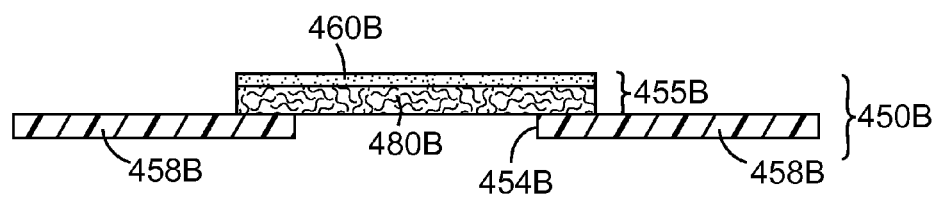

FIG. 4B shows an embodiment of a filter assembly 450B having composite filter body 455B mounted across filter assembly aperture 454B, the composite filter body 455B contacting only one major surface of filter support layer 458B, and wherein water-absorbent layer 480B is positioned between microporous membrane 460B and the major surface of filter support layer 458B.

Figure 4C:
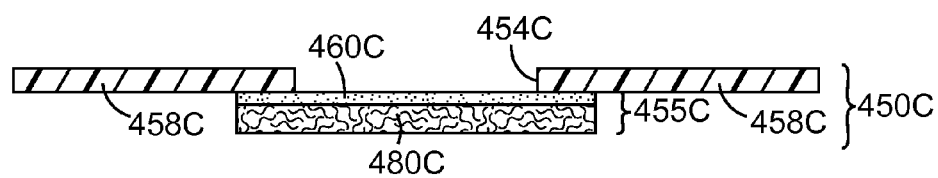

FIG. 4C shows an embodiment of a filter assembly 450C having composite filter body 455C mounted across filter assembly aperture 454C, the composite filter body 455C contacting only one major surface of filter support layer 458C, and wherein microporous membrane 460C is positioned between water-absorbent layer 480C and the major surface of filter support layer 458C.

Figure 4D:
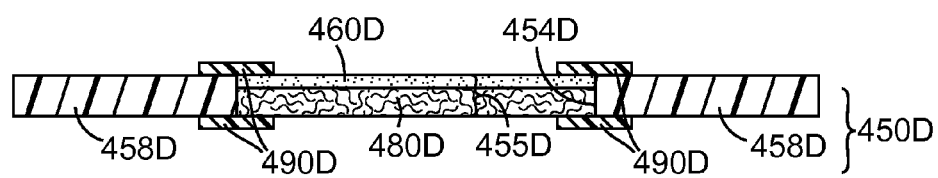

FIG. 4D shows an embodiment of a filter assembly 450D, wherein a perimeter of the composite filter body 455D fits within filter assembly aperture 454D.

In any of the embodiments in FIGS. 1A and 4A-4D, at least one gasket may be provided to mount the composite filter body 155 (or 455A-D) onto the filter support layer 158 (or 458A-D), as is shown, for example, in FIG. 4D, where at least one gasket 490D may be provided to secure the composite filter body 455D to filter support layer 458D. The gasket may be of any suitable material, for example, biaxially-oriented polypropylene (BOPP), and may further comprise a layer of an adhesive to affix to both the composite filter body 155 (or 455A-D) and the filter support layer. In the embodiment shown in FIG. 1A, for example, a first gasket (not shown in FIG. 1A) may be provided to mount microporous membrane 160 onto a first major surface of the filter support layer 158, and a second gasket (not shown in FIG. 1A) may be provided to mount water-absorbent layer 180 onto a second major surface of the filter support layer 158.

A person of ordinary skill in the art will recognize that additional techniques for mounting the components of composite filter body 155 onto the filter support layer 158 may be suitable, including, for example, adhesives, heat-bonding, ultrasonic welding, or combinations of these.

The microporous membrane 160 (or any of microporous membranes 460A-D) can comprise any one of a variety of water-permeable microporous membrane materials known in the art including, for example, cellulosic membranes (e.g., cellulose acetate, mixed cellulose esters, and nitrocellulose), nylon, polycarbonate, polyethersulfone, polyester, polyvinylidene fluoride, ceramic, a derivative of any of the foregoing, and a combination of any two or more of the foregoing. The nominal pore size of the microporous membrane 160 is typically selected according to microorganisms to be detected. For example, a nominal pore size in a range of 0.05 micrometer to 1.2 micrometer (including any of 0.05 micrometer, 0.1 micrometer, 0.2 micrometer, 0.45 micrometer, 0.8 micrometer, or 1.2 micrometer), or in some embodiments a range of 0.2 micrometer to 0.45 micrometer, can be used to detect bacteria. In some embodiments, a nominal pore size in a range of 0.05 micrometer to 3 micrometers (including any of 0.45 micrometer, 0.8 micrometer, 1.2 micrometer, or 3 micrometers), or in some embodiments a range of 0.45 micrometer to 1.2 micrometer, can be used to detect yeast and/or molds. In any embodiment, the microporous membrane should be configured to collect microorganisms from an aqueous sample filtered through the filter assembly. Water permeability test measurements may include, for example, those described in ASTM F2298-03.

Examples of useful commercial microporous membranes include cast nylon microporous membranes available from 3M Purification, Inc. (Meriden, Conn.) under the trade designations "LIFEASSURE" and "STERASSURE". Useful microporous membranes are described, for example, in U.S. Pat. No. 6,413,070 (Meyering et al.), U.S. Pat. No. 6,513,666 (Meyering et al.), U.S. Pat. No. 6,776,940 (Meyering et al.), U.S. Pat. No. 6,056,529 (Meyering et al.), U.S. Pat. No. 6,264,044 (Meyering et al.), U.S. Pat. No. 5,006,247 (Dennison et al.), U.S. Pat. No. 3,876,738 (Marinaccio et al.), U.S. Pat. No. 4,707,265 (Barnes et al.), and U.S. Pat. No. 4,473,474 (Ostreicher et al.). Useful graft polymer functionalized microporous membranes are described, for example, in U.S. Published Pat. App. No. 2010/0261801 (Weiss et al.), published Oct. 14, 2010.

In some embodiments of article 100, the water-absorbent layer 180 in the composite filter body 155 comprises a fibrous substrate that is functionalized with a grafted hydrogel polymer. In some embodiments, the fibrous substrate is a nonwoven substrate. As used herein, the term "nonwoven" means a textile structure produced by bonding or interlocking of fibers, or both, accomplished by mechanical, chemical, thermal, or solvent means and combinations in accordance with ASTM D123-09e1.

In some embodiments, the water-absorbent layer 180 can comprise a fibrous substrate that is a woven substrate functionalized with a grafted hydrogel polymer. "Woven substrate" as used herein can include cloths or fabrics. As used herein, "woven" means a structure produced when at least two sets of strands are interlaced, usually at right angles to each other, according to a predetermined pattern of interlacing, and such that at least one set is parallel to the axis along the lengthwise direction of the fabric, in accordance with ASTM D123-09e1. These substrates are typically made from natural fibers (e.g., cotton or wool), synthetic fibers (e.g., nylon, polyester, acrylonitrile), or blends thereof. While the grafting chemistry described herein is primarily in terms of nonwoven substrates, it will be understood that the grafting chemistry can also be applied to woven substrates for use as the water-absorbent layer 180 in the microbial detection article 100.

The fibrous substrate may have an average fiber size in a range from 0.7 micrometer to 15 micrometers, and a void volume in a range from 50% to 95%.

The grafted hydrogel polymer includes grafting monomer units grafted to the surface of the fibrous substrate, wherein the grafting monomer units are selected from the group consisting of ionic grafting monomer units, non-ionic hydrophilic monomer units, and mixtures thereof. In some embodiments, the grafted hydrogel polymer is a cationic hydrogel polymer comprising cationic aminoalkyl(meth)acryloyl monomer units (described infra), such as (3-[(methacryloylamino)propyl]trimethylammonium chloride) (MAPTAC), grafted to the surface of the fibrous substrate. In some other embodiments, the grafted hydrogel polymer is an anionic hydrogel polymer, comprising anionic monomer units (described infra), such as 2-acrylamido-2-methylpropanesulfonic acid (AMPS), grafted to the surface of the fibrous substrate. In some other embodiments, the grafted hydrogel polymer is a non-ionic hydrogel polymer, comprising non-ionic hydrophilic monomer units (described infra), such as dimethylacrylamide (DMA) or 2-hydroxyethyl(meth)acrylate (HEMA), grafted to the surface of the fibrous substrate. In some embodiments the grafted hydrogel polymer is a combination of cationic aminoalkyl(meth)acryloyl monomer units and anionic monomer units grafted to the surface of the fibrous substrate. In some embodiments, the grafted hydrogel polymer is a combination of ionic (cationic and/or anionic) and non-ionic hydrophilic monomers grafted to the surface of the fibrous substrate.

In some embodiments, the fibrous substrate includes a nonwoven web which may include nonwoven webs manufactured by any of the commonly known processes for producing nonwoven webs. As used herein, the term "nonwoven web"

refers to a fabric that has a structure of individual fibers or filaments which are randomly and/or unidirectionally interlaid in a mat-like fashion.

For example, the nonwoven web can be made by carded, air laid, wet laid, spunlaced, spunbonding, electrospinning or melt-blowing techniques, such as melt-spun or melt-blown, or combinations thereof. Spunbonded fibers are typically small diameter fibers that are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g., air) stream which attenuates the filaments of molten thermoplastic material to reduce their diameter. Thereafter, the meltblown fibers are carried by the high velocity gas stream and are deposited on a collecting surface to from a web of randomly disbursed meltblown fibers. Any of the nonwoven webs may be made from a single type of fiber or two or more fibers that differ in the type of thermoplastic polymer and/or thickness.

Staple fibers may also be present in the web. The presence of staple fibers generally provides a loftier, less dense web than a web of only melt blown microfibers. Preferably, no more than 20 weight percent staple fibers are present, more preferably no more than 10 weight percent. Such webs containing staple fiber are disclosed in U.S. Pat. No. 4,118,531 (Hauser).

The fibrous substrate may optionally further include, for example, one or more layers of scrim. For example, either or both of the major surfaces may optionally comprise a scrim layer. The scrim, which is typically a woven or nonwoven reinforcement made from fibers, is included to provide strength to the nonwoven substrate. Suitable scrim materials include, but are not limited to, nylon, polyester, fiberglass, and the like. The average thickness of the scrim can vary. Typically, the average thickness of the scrim is in a range from 25 micrometers to 100 micrometers, or in some embodiments a range from 25 micrometers to 50 micrometers. The layer of the scrim may optionally be bonded to the nonwoven substrate. A variety of adhesive materials can be used to bond the scrim to the polymeric material. Alternatively, the scrim may be heat-bonded to the nonwoven substrate.

The microfibers of the nonwoven substrate typically have an effective fiber diameter of from 0.5 micrometer to 15 micrometers, preferably from 1 micrometer to 6 micrometers, as calculated according to the method set forth in Davies, C. N., "The Separation of Airborne Dust and Particles," Institution of Mechanical Engineers, London, Proceedings 1B, 1952. The nonwoven substrate preferably has a basis weight in the range of 10 to 400 g/m² (grams per meter squared), more preferably 10 to 100 g/m². The average thickness of the nonwoven substrate is preferably 0.1 millimeter to 10 millimeters, more preferably 0.25 millimeter to 5 millimeters for the non-functionalized, uncalendered substrate. The minimum tensile strength of the nonwoven web is about 4 Newtons. It is generally recognized that the tensile strength of nonwovens is lower in the machine direction than in the cross-web direction due to better fiber bonding and entanglement in the latter.

Nonwoven web loft is measured by solidity, a parameter that defines the solids fraction in a volume of web. Lower solidity values are indicative of greater web loft. Useful nonwoven substrates have a solidity of less than 20%, preferably less than 15%. Solidity is a unitless fraction typically represented by α:

$$\alpha = m_f \div \rho_f \times L_{nonwoven}$$

where $m_f$ is the fiber mass per sample surface area, which $\rho_f$ is the fiber density; and $L_{nonwoven}$ is the nonwoven thickness. Solidity is used herein to refer to the nonwoven substrate itself and not to the functionalized nonwoven. When a nonwoven substrate contains mixtures of two or more kinds of fibers, the individual solidities are determined for each kind of fiber using the same $L_{nonwoven}$ and these individual solidities are added together to obtain the web's solidity, α.

In some embodiments, the nonwoven substrate has a mean pore size of 1 micrometer to 40 micrometers, or in some embodiments even 2 micrometers to 20 micrometers. Mean pore size may be measured according to ASTM F316-03 Standard Test Methods for Pore Size Characteristics of Membrane Filters by Bubble Point and Mean Flow Pore Test Method B using a test fluid available from DuPont (Wilmington, Del.) under the trade designation "FREON TF".

The nonwoven substrate may be formed from any suitable thermoplastic polymeric material. Suitable polymeric materials include, but are not limited to, polyolefins, poly(isoprenes), poly(butadienes), fluorinated polymers, chlorinated polymers, polyamides, polyimides, polyethers, poly(ether sulfones), poly(sulfones), poly(vinyl acetates), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

Suitable polyolefins for the nonwoven substrate include, but are not limited to, poly(ethylene), poly(propylene), poly (1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers for the nonwoven substrate include, but are not limited to, poly(vinyl fluoride), poly (vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides for the nonwoven substrate include, but are not limited to, nylon 6, nylon 6,6, nylon 6,12 poly (iminoadipoyliminohexamethylene), poly(iminoadipoyliminodecamethylene), and polycaprolactam. Suitable polyimides include poly(pyromellitimide).

Suitable poly(ether sulfones) for the nonwoven substrate include, but are not limited to, poly(diphenylether sulfone) and poly(diphenylsulfone-co-diphenylene oxide sulfone).

Suitable copolymers of vinyl acetate for the nonwoven substrate include, but are not limited to, poly(ethylene-co-vinyl acetate) and such copolymers in which at least some of the acetate groups have been hydrolyzed to afford various poly(vinyl alcohols) including, poly(ethylene-co-vinyl alcohol).

In some embodiments, the polymers for the nonwoven substrate are inherently hydrophilic and are readily grafted by ionizing radiation, such as e-beam or gamma radiation. Useful polymers include polyamides and ethylene vinyl alcohol polymers and copolymers. Nylon nonwoven substrates having 1 micrometer or smaller effective fiber diameters may be chosen from those described, for example, in U.S. Pat. No. 7,170,739 (Arora et al.), U.S. Pat. No. 7,112,389 (Arora et al.), U.S. Pat. No. 7,235,122, (Bryner et al.), and U.S. Published Pat. App. No. 2004/0116026. Useful nylon nonwoven substrates having 1 micrometer or smaller effective fiber diameters include, for example, hybrid membrane technology membranes available from DuPont (Wilmington, Del.) under the trade designations "HMT 16434" and "HMT 16435".

Further details on the manufacturing method of nonwoven substrates of this description may be found, for example, in Wente, Superfine Thermoplastic Fibers, 48 Indus. Eng. Chem. 1342 (1956), or in Wente et al., Manufacture Of Superfine Organic Fibers, (Naval Research Laboratories Report No. 4364, 1954). Useful methods of preparing the nonwoven substrates are described, for example, in U.S. Pat. No. RE39, 399 (Allen), and U.S. Pat. No. 3,849,241 (Butin et al.), U.S. Pat. No. 7,374,416 (Cook et al.), U.S. Pat. No. 4,936,934 (Buehning), and U.S. Pat. No. 6,230,776 (Choi).

In typical embodiments, the grafted hydrogel polymer comprises polymer chains (tendrils) that are initiated from, and supported by, the nonwoven substrate, the polymer tendrils extending into the interstitial spaces of the nonwoven substrate. In some embodiments of the nonwoven substrate, the grafted hydrogel polymer chains have pendent groups that are cationic. In some other embodiments of the nonwoven substrate, the grafted hydrogel polymer chains have pendent groups that are anionic. In some embodiments of the nonwoven substrate, the grafted hydrogel polymer chains have pendant groups that are non-ionic hydrophilic functional groups (described infra). In the presence of pure water the hydrogel reaches a state of maximum hydration and volume. As the polymer tendrils may be free to move independently, the nonwoven substrate having the grafted hydrogel polymer may have a large flow response to very low quantities of stimulus.

Depending on the degree of substitution of the nonwoven substrate and the weight of hydrogel polymer grafted to the surface thereof, the grafted hydrogel polymer can completely fill the interstitial spaces of the nonwoven substrate thereby providing a barrier which effectively blocks the flow of pure water through the functionalized nonwoven article. The grafted hydrogel polymer, which may be considered to exist as a hydrogel network, can reversibly expand in response to a very small amount of a "trigger" such as a salt, a buffer, an organic solvent, a temperature, or a pH, consequently contracting and thereby allowing for higher flux at lower pressure through the hydrogel network. In the absence of such a "trigger", the fully expanded hydrogel network can offer resistance to water flux.

In the state of maximum hydration, the grafted hydrogel polymer is constrained only by the nonwoven substrate, most significantly in the x and y axes (coplanar with the nonwoven substrate) and less so in the z axis, normal to the plane of the nonwoven substrate. The grafted hydrogel polymer is less constrained on the z axis. The grafted hydrogel polymer may swell up to 800 percent or more on the z axis, but the x and y axes desirably swell less than 100%, more preferably less than 50%, constrained by the nonwoven substrate.

In the preparation of melt-blown nonwoven webs conditions can be adjusted to maximize the resiliency in the z direction (normal to the plane of the nonwoven by (a) adjusting the die and collector for proper fiber lay-down (b) adjusting melt temp and air temp to prevent fibers from over-fusing and forming fiber-fiber bonds, (c) minimize asymmetry caused by the collector being too close in proximity to the die. It is preferred that nonwoven fibers are below the polymer melt temperature before impinging on the collector to reduce the degree of fiber-fiber links. Desirably, the nonwoven substrate may expand maximally in "z" direction (normal to the plane of the nonwoven) to allow for expansion of the grafted hydrogel polymer.

The grafted hydrogel polymer reversibly contracts and allows water to flow (flux) through the resulting interstices in the presence of dissolved species, such as neutral compounds, salts, and buffers. Without being bound by theory, it is believed that when pendant groups in the grafted hydrogel polymer include ionized groups, the dissolved species such as dissolved ions more effectively charge-couple to the ionized groups in the pendant groups in the graft hydrogel polymer so that the electrostatic repulsion between the ionized groups are reduced and the hydrogel constricts or collapses. When the ionized groups in the pendant groups in the grafted hydrogel polymer are anionic, the addition of negatively charged ions dissolved in water results in reversible contraction of the hydrogel, potentially by reducing electrostatic repulsion between the negatively charged anionic groups. Similarly, when the ionized groups in the pendant groups in the graft polymer are cationic, the addition of positively charged ions dissolved in water results in reversible contraction of the hydrogel, potentially by reducing electrostatic repulsion between the positively charged cationic groups (e.g., quaternary ammonium groups). Alternatively the dissolved species may displace the hydration sphere of the water (and possible solvent) molecules with the result that the hydrogel collapses around the nonwoven substrate. Therefore the article exhibits a stimulus-response hydrogel ("responsive hydrogel") that is discontinuous in nature—able to reversibly open and close the pores or interstices of the hydrogel.

In some embodiments, the nonwoven substrate has an ionic grafted hydrogel polymer comprising anionic monomer units grafted to the surface of the nonwoven substrate. The hydrogel polymer is grafted to the surface(s) of the nonwoven substrate by ionization initiated polymerization of "ionic grafting monomers" that are anionic (i.e., negatively charged). Examples of useful nonwoven substrates comprising anionic monomer units grafted to the surface of the nonwoven substrate, and methods of grafting, are described, for example, in International Patent Application No. PCT/US2010/038488 (Waller et al.).

The anionic monomer has at least one ethylenically unsaturated group capable of undergoing free radical polymerization, and an additional anionic functional group. In some embodiments, the ethylenically unsaturated group is a (meth) acryloyl group or a vinyl group. The anionic monomer can be a weak acid, a strong acid, a salt of a weak acid, a salt of a strong acid, or combinations thereof. That is, the anionic monomer can be in a neutral state but capable of being charged if the pH is adjusted. When the pH is suitably adjusted, the resulting graft materials have negatively charged groups capable of interacting with positively charged materials (i.e., cations). If the anionic monomer includes a salt of a weak acid or a salt of a strong acid, the counter ions of these salts can be, but are not limited to, alkali metals, alkaline earth metals, ammonium ions, or tetraalkylammonium ions.

The anionic monomers may have the general Formula (I):

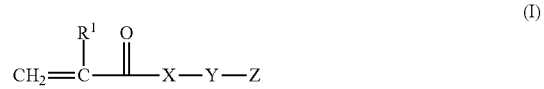

(I)

where
$R^1$ is H or $CH_3$;
X is —O— or —$NR^1$—,
Y is a straight or branched chain alkylene, generally from 1 to 10 carbon atoms; and Z is an anionic group, which may be selected from sulphonic acids groups, phosphonic acid groups, and carboxylic acid groups, and salts thereof.

Some exemplary anionic monomers include (meth)acrylamidosulfonic acids of Formula (II) or salts thereof:

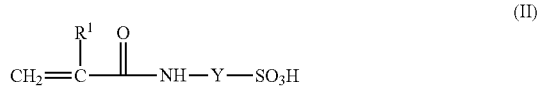

(II)

where $R^1$ is H or $CH_3$, and Y is a straight or branched alkylene having 1 to 10 carbon atoms. Exemplary anionic monomers according to Formula (II) include, but are not limited to, N-acrylamidomethanesulfonic acid, 2-acrylamidoethanesulfonic acid, 2-acrylamido-2-methylpropanesulfonic acid (AMPS), and 2-methacrylamido-2-methylpropanesulfonic acid. Salts of these acidic monomers can also be used, examples being (3-sulfopropyl)-methacrylic acid potassium salt and 2-(methacryloyloxy)ethylsulfonic acid sodium salt.

Other suitable anionic monomers for the graft hydrogel polymer include sulfonic acids such as vinylsulfonic acid and 4-styrenesulfonic acid; (meth)acrylamidophosphonic acids such as (meth)acrylamidoalkylphosphonic acids (e.g., 2-acrylamidoethylphosphonic acid and 3-methacrylamidopropylphosphonic acid); acrylic acid and methacrylic acid; and carboxyalkyl(meth)acrylates such as 2-carboxyethylacrylate, 2-carboxyethylmethacrylate, 3-carboxypropylacrylate, and 3-carboxypropylmethacrylate. Still other suitable acidic monomers include (meth)acryloylamino acids, such as those described in U.S. Pat. No. 4,157,418 (Heilmann). Exemplary (meth)acryloylamino acids include, but are not limited to, N-acryloylglycine, N-acryloylaspartic acid, N-acryloyl-β-alanine, 2-acrylamidoglycolic acid, 3-acrylamido-3-methylbutyric acid. Salts of any of these acidic monomers can also be used.

In some embodiments, the nonwoven substrate has an ionic hydrogel polymer comprising cationic monomer units grafted to the surface of the nonwoven substrate. The polymer is grafted to the surface(s) of the nonwoven substrate by ionization initiated polymerization of "ionic grafting monomers" that are cationic (i.e., positively charged). Examples of useful nonwoven substrates comprising cationic monomer units grafted to the surface of the nonwoven substrate, and methods of grafting, are described, for example, in U.S. Published Pat. App. No. 2010/0155323 (Weiss et al., published Jun. 24, 2010).

In some embodiments, the cationic monomer units are aminoalkyl(meth)acryloyl monomer units grafted to the surface of the nonwoven substrate. The polymer is grafted to the surface(s) of the nonwoven substrate by e-beam initiated polymerization of grafting monomers, which include aminoalkyl(meth)acryloyl monomers.

The grafting aminoalkyl(meth)acryloyl monomers are amino(meth)acrylates or amino(meth)acrylamides of Formula (III) or quaternary ammonium salts thereof.

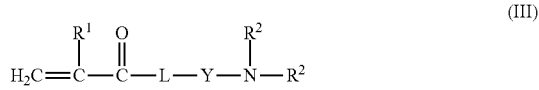

(III)

In Formula (III), $R^1$ is hydrogen or methyl, preferably methyl; L is —O— or —NH—; and Y is an alkylene (e.g., an alkylene having 1 to 10 carbon atoms, 1 to 6, or 1 to 4 carbon atoms). Each $R^2$ is independently hydrogen or alkyl, preferably $C_1$-$C_4$ alkyl. Alternatively, the two $R^2$ groups taken together with the nitrogen atom to which they are attached can form a heterocyclic group that is aromatic, partially unsaturated (i.e., unsaturated but not aromatic), or saturated, wherein the heterocyclic group can optionally be fused to a second ring that is aromatic (e.g., benzene), partially unsaturated (e.g., cyclohexene), or saturated (e.g., cyclohexane). The counter ions of the quaternary ammonium salts may include, for example, halides, sulfates, phosphates, and nitrates. Such grafting monomers may be quaternary ammonium monomers (i.e., having a —$N(R^2)_3{}^+X^-$ group), wherein each $R^2$ is as defined, an $X^-$ is the counter anion. Such monomers having a quaternary ammonium group may be directly grafted to the surface of the nonwoven substrate or a grafting aminoalkyl (meth)acryloyl monomer, having a primary, secondary or tertiary amine group, may be grafted and subsequently converted to a quaternary ammonium group by alkylation.

In some embodiments of Formula (III), both $R^2$ groups are hydrogen. In other embodiments, one $R^2$ group is hydrogen and the other is an alkyl having 1 to 10, 1 to 6, or 1 to 4 carbon atoms. In yet other embodiments, the $R^2$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to imidazolyl, piperazinyl, and morpholinyl. The heterocyclic group can be fused to an additional ring such as a benzene, cyclohexene, or cyclohexane. Exemplary heterocyclic groups fused to an additional ring include, but are not limited to, benzoimidazolyl.

Exemplary aminoalkyl(meth)acrylates (i.e., L in Formula (III) is oxy) include N,N-dialkylaminoalkyl(meth)acrylates such as, for example, N,N-dimethylaminoethylmethacrylate, N,N-dimethylaminoethylacrylate, N,N-diethylaminoethylmethacylate, N,N-diethylaminoethylacrylate, N,N-dimethylaminopropylmethacrylate, N,N-dimethylaminopropylacrylate, N-tert-butylaminopropylmethacrylate, N-tert-butylaminopropylacrylate and the like.

Exemplary amino(meth)acrylamides (i.e., L in Formula (III) is —NH—) include, for example, N-(3-aminopropyl)methacrylamide, N-(3-aminopropyl)acrylamide, N-[3-(dimethylamino)propyl]methacrylamide, N-methyl-N'-acryloylpiperazine, N-(3-imidazolylpropyl)methacrylamide, N-(3-imidazolylpropyl)acrylamide, N-(2-imidazolylethyl)methacrylamide, N-(1,1-dimethyl-3-imidazoylpropyl)methacrylamide, N-(1,1-dimethyl-3-imidazoylpropyl)acrylamide, N-(3-benzoimidazolylpropyl)acrylamide, and N-(3-benzoimidazolylpropyl)methacrylamide.

Exemplary quaternary salts of the aminoalkyl(meth)acryloyl monomers of Formula (III) include, but are not limited to, (meth)acrylamidoalkyltrimethylammonium salts (e.g., 3-[(methacryloylamino)propyl]trimethylammonium chloride (MAPTAC) and 3-[(acryloylamino)propyl]trimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

In some embodiments, the nonwoven substrate has a hydrogel polymer comprising non-ionic monomer units grafted to the surface of the nonwoven substrate. The non-ionic grafted polymer contains ethylenically-unsaturated hydrophilic grafting monomer units; "non-ionic hydrophilic monomers". As used herein, "non-ionic hydrophilic monomers" are those polymerizable monomers having a water miscibility (water in monomer) of at least 1 weight percent (in some embodiments, at least 2 weight percent, or at least 3 weight percent, or at least 4 weight percent), or in some embodiments preferably at least 5 weight percent without reaching a cloud point. These monomers contain no groups that would retard the grafting polymerization. Examples of suitable non-ionic hydrophilic monomers include 2-hydroxyethyl(meth)acrylate (HEMA), 2-hydroxypropyl(meth)acrylate, 3-hydroxypropyl(meth)acrylate, 2,3-dihydroxypropyl (meth)acrylate, 4-hydroxybutyl(meth)acrylate, N-vinyl caprolactam, N-vinyl acetamide, N-vinyl pyrrolidone, acrylonitrile, tetrahydrofurfuryl acrylate, acrylamide, mono- or di-N-alkyl substituted acrylamide, glycerol methacrylate, and combinations thereof. Preferred non-ionic hydrophilic monomers include 2-hydroxyethyl(meth)acrylate (HEMA), N-vinyl pyrrolidone, N-vinyl acetamide, methylacrylamide, dimethylacrylamide (DMA), and mixtures thereof.

In some embodiments, the non-ionic hydrophilic monomers are monofunctional ethylenically-unsaturated grafting monomer units having a poly(alkylene oxide) group. The monomer units having a poly(alkylene oxide) group is of the Formula (IV):

wherein Z is a polymerizable ethylenically unsaturated moiety, $R^1$ is a H or $CH_3$, $R^2$ is a H, a $C_1$ to $C_4$ alkyl group, aryl group, or combinations thereof and m is from 2 to 100, preferably 5 to 20, and Q is a divalent linking group selected from —O—, —$NR^1$—, —$CO_2$— and —$CONR^1$.

In one embodiment, the poly(alkylene oxide) group is a poly(ethylene oxide) (co)polymer. In another embodiment, the pendent poly(alkylene oxide) group is a poly(ethylene oxide-co-propylene oxide) copolymer. Such copolymers may be block copolymers, random copolymers, or gradient copolymers.

Useful ethylenically unsaturated moiety, Z, of the monomer may include:

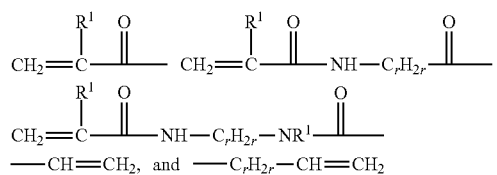

wherein $R^1$ is H or Me and r=1-10.

The monomer having a poly(alkylene oxide) group can be prepared, for example, by reacting mono- or di-functional alkylene oxide (co)polymers (which are typically commercially available) with reactive ethylenically unsaturated compounds (e.g., acrylates). The functional groups terminating the poly(alkylene oxide) may include hydroxy groups, amine groups and carboxyl groups. A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl(meth)acrylate. Preferably, the monomer is prepared by reacting the mono- or di-functional alkylene oxide (co)polymer with (meth)acrylic anhydride. Typically, if a stoichiometric amount of the ethylenically unsaturated reactant is combined with the monofunctional alkylene oxide (co)polymer (such as a monohydroxy terminated alkylene oxide (co)polymer), 100% conversion to the monosubstituted product is obtained.

Examples of suitable monofunctional poly(alkylene oxide) monomers include poly(ethylene oxide) (meth)acrylate, polypropylene oxide) (meth)acrylate, poly(ethylene oxide-propylene oxide) (meth)acrylate, and combinations thereof. Such monomers preferably include one nonreactive end group such as ($C_1$-$C_4$) alkoxy, aryloxy (e.g., phenoxy), and ($C_1$-$C_4$) alkaryloxy. These groups can be linear or branched. These monomers can be of a wide range of molecular weights and are commercially available from sources such as Sartomer Company (Exton, Pa.); Shinnakamura Chemical Co., Ltd. (Tokyo, Japan); Aldrich (Milwaukee, Wis.); and Osaka Organic Chemical Ind., Ltd. (Osaka, Japan).

Typically, the grafted hydrogel polymer is uncrosslinked, and the imbibing solution containing the monomer mixture contains no polyethylenically unsaturated monomers (i.e., no crosslinkers).

In some embodiments, the grafted hydrogel polymer comprises ionic grafting monomers and/or non-ionic hydrophilic grafting monomers in any suitable combination of weight percentages totaling 100 weight percent, including the extreme values of 100 weight percent ionic grafting monomer or 100 weight percent non-ionic hydrophilic grafting monomer, as well combinations of ionic grafting monomers (cationic and/or anionic) and non-ionic hydrophilic grafting monomers any suitable amounts between these extremes, including, for example, having ionic grafting monomer in an amount of at least 1 weight percent, or at least 2 weight percent, or at least 5 weight percent, or at least 10 weight percent, or at least 30 weight percent, or at least 50 weight percent, or at least 70 weight percent, or at least 80 weight percent, or at least 90 weight percent, or at least 95 weight percent, or at least 98 weight percent, or even at least 99 weight percent, the remainder being non-ionic hydrophilic grafting monomer, each weight percentage relative to the weight of total monomer content.

In some embodiments, the total grafted monomer content may be from 0.5 to 5 times the weight of the nonwoven substrate. It is desirable to fill the interstitial spaces of the nonwoven substrate but not have the polymer chains bridge to link separate fibers of the nonwoven with grafted polymer strands, as this will restrict expansion of the nonwoven substrate and impede flux. One way to reduce this fiber-fiber bridging by the grafted polymer is to lower the monomer concentration for a given fiber size. It has been determined that the amount and the morphology of the grafted hydrogel polymer may be influenced by adding a water miscible organic solvent to the grafting imbibing solution to control the molecular weight of the grafted hydrogel polymer tendrils and reduce bridging of the tendrils.

The grafting of a hydrogel polymer onto the nonwoven substrate enhances water-absorption capacity of the water-absorbent layer 180 of the current disclosure, which can be measured in terms of multiples of a weight of the grafted nonwoven substrate. In some embodiments, the water-absorbent layer 180 comprising a nonwoven substrate having a grafted hydrogel polymer of the current description can absorb a weight of water that is at least 0.5 times, at least 1 time, at least 2 times, at least 3 times, at least 4 times, at least 5 times, at least 10 times, at least 15 times, at least 20 times, or even at least 30 times the weight of the water-absorbent layer 180 prior to absorbing water. The enhanced water-absorption capacity is useful for retaining an aliquot of water from an aqueous sample that is passed through the water-absorbent layer 180, because a portion of the aliquot of water can be in fluid communication with microorganisms, water-soluble gelling agent, nutrients, and detection agents when present in the microbial detection article 100, in order to support growth and detection of microorganisms (if present). In some commercially available thin film culture devices, including those available from 3M Company (St. Paul, Minn.) under the trade designation "PETRIFILM", a typical protocol calls for the addition of about 1 milliliter of water to the thin film culture device in order to support the growth and detection of microorganisms, whereas in the microbial detection article of the current description, filtration of an aqueous sample through the water-absorbent layer 180 provides all of the water needed for the support the growth and detection of microorganisms. In some embodiments of the microbial detection article 100, it may be desirable for the water-absorbent layer 180 to retain an aliquot of water from an aqueous sample wherein the volume of the aliquot of water is in a range from 0.1 milliliters to 2 milliliters, or from 0.3 to 1.5 milliliters, or from 0.5 to 1.5 milliliters, or from 0.7 to 1.3 milliliters, or from 0.8 to 1.2 milliliters, or even from 0.9 to 1.1 milliliters.

With regard to the grafting monomers supra, the monomers that are grafted to the surface of the nonwoven substrates usually have either an acrylate or other non-acrylate polymerizable functional group for grafting by e-beam irradiation. Acrylamide or methacrylate groups are preferred for grafting of the monomer to the nonwoven substrate surface (using the process described herein) due to the slower, more uniform reactivity and durability of such methacrylates or acrylamido moieties to nonwovens that have been exposed to e-beam irradiation.

As described in further detail below, functionalized substrates of the present disclosure may be prepared using above-described monomers to provide a grafted polymer on the surface of a porous nonwoven base substrate. When two or more of the above-described grafting monomers are used, the monomers may be grafted onto the nonwoven base substrate in a single reaction step (i.e., exposure to an ionizing radiation) followed by imbibing with all grafting monomers present or in sequential reaction steps (i.e., a first exposure to ionizing radiation followed by imbibing with one or more grafting monomer, then a second exposure to an ionizing radiation and a second imbibing after the second exposure to the ionizing radiation).

It will be further understood that the grafting process will yield a radical species on the surface of the nonwoven substrate. In some typical embodiments, after imbibing the nonwoven substrate with a solution containing a mixture of ionic and non-ionic grafting monomers, polymerization will initiate with the formation of a radical on the carbon alpha to the carbonyl of any one of the grafting monomers. The radical so formed may further polymerize with one or more additional grafting monomers, resulting in a grafted polymers having these groups pendent from the polymer chain as simply illustrated below.

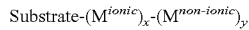
Substrate-$(M^{ionic})_x$-$(M^{non-ionic})_y$

In the formula, the -$(M^{ionic})_x$- represents the residue of the ionic grafting monomers of one of Formula (I), Formula (II), or Formula (III) having "x" polymerized ionic grafting monomer units, and the -$(M^{non-ionic})_y$ represents the polymerized non-ionic hydrophilic monomers, having y polymerized monomer units. The polymer may be random or block. The polymer may be directly grafted via the residue of the -$(M^{ionic})$- monomer, as shown, or may be directly grafted via the -$(M^{non-ionic})$-non-ionic hydrophilic monomer.

The values of the subscripts x and y may be an integral or non-integral value and correspond to the amount of each monomer in the imbibing solution previous described. For example, in some embodiments the value of the subscript "x" will correspond to an amount of from 70 weight percent to 100 weight percent of the ionic grafting monomers in the imbibing solution, and the value of subscript y will correspond to an amount of from 30 weight percent to 10 weight percent of the non-ionic hydrophilic monomers.

In some other embodiments, the nonwoven substrate may be grafted exclusively with non-ionic monomers selected from the "non-ionic hydrophilic monomers" described above, to provide a nonwoven substrate having a non-ionic grafted hydrogel polymer, and the value of the subscript y will correspond to 100 weight percent of the non-ionic hydrophilic monomers, and the values of the x subscript will correspond to 0 weight percent.

It will be understood that various combinations of values for the subscripts x and y may be used in order to provide a nonwoven substrate having a grafted hydrogel that is capable of maintaining a water activity ($A_w$) value of greater than 0.91 for article 100 in the methods described herein for using the article 100.

The process of preparing the grafted nonwoven substrate comprises providing a nonwoven substrate, exposing the nonwoven substrate to e-beam radiation in an inert atmosphere, and subsequently imbibing the exposed substrate with a solution comprising grafting monomers to graft polymerize said grafting monomers to the surface of the nonwoven substrate. Suitable methods for preparing the grafted nonwoven substrate include those described, for example, in U.S. Published Pat. App. Nos. 2007/0154651 (Weiss et al.) and 2010/0075560 (Seshadri et al.).

In some embodiments of radiation grafting, the first step includes exposing the nonwoven substrate to ionizing radiation, such as e-beam radiation, in an inert atmosphere. Generally, the substrate is placed in a chamber purged of oxygen. Typically, the chamber comprises an inert atmosphere such as nitrogen, carbon dioxide, helium, argon, etc., with a minimal amount of oxygen (less than 100 ppm), which is known to inhibit free-radical polymerization.

The irradiation step comprises the ionizing irradiation of nonwoven substrate surfaces, preferably with ionizing e-beam or gamma radiation to prepare free radical reaction sites on such surfaces upon which the monomers are subsequently grafted. "Ionizing irradiation" means radiation of a sufficient dosage and energy to cause the formation of free radical reaction sites on the surface(s) of the base substrate. Ionizing radiation may include gamma, electron-beam, x-ray and other forms of electromagnetic radiation. In some instances, corona radiation can be sufficiently high energy radiation. The radiation is sufficiently high energy, that when absorbed by the surfaces of the base substrate, sufficient energy is transferred to that support to result in the cleavage of chemical bonds in that support and the resultant formation of free radical sites on the nonwoven substrate. One or more layers of nonwoven substrates may be subjected to the ionizing radiation.

High energy radiation dosages are measured in units of kilogray (kGy). Doses can be administered in a single dose of the desired level or in multiple doses which accumulate to the desired level. Dosages can range cumulatively from 1 kGy to 200 kGy. The dose can be delivered all at once such as from an E-beam source or accumulated from a slow dose rate over several hours such as dosage delivered from a gamma source. Preferably, the cumulative dosage exceeds 20 kGy (2 Mrads) for substrates resistant to radiation damage.

Electron beam is one preferred method of grafting due to the ready-availability of commercial sources. Electron beam generators are commercially available from a variety of sources, including the electron beam generator available from Energy Sciences, Inc. (Wilmington, Mass.) under the trade designation "ESI ELECTROCURE EB SYSTEM", and including the electron beam generator available from PCT Engineered Systems, LLC (Davenport, Iowa) under the trade designation "BROADBEAM EB PROCESSOR". For any given piece of equipment and irradiation sample location, the dosage delivered can be measured in accordance with ASTM E-1275 entitled "Practice for Use of a Radiochromic Film Dosimetry System."

Dose is the total amount of energy absorbed per mass unit. Generally, it was found that doses in the range of 20 to 40 kGy were suitable for generating the grafted hydrogel polymer.

Other sources of irradiation, such as gamma radiation sources, may be used with equal grafting performance. Generally, suitable gamma ray sources emit gamma rays having energies of 400 keV or greater. Typically, suitable gamma ray sources emit gamma rays having energies in the range of 500 keV to 5 MeV. Examples of suitable gamma ray sources include cobalt-60 isotope (which emits photons with energies of approximately 1.17 and 1.33 MeV in nearly equal proportions) and cesium-137 isotope (which emits photons with energies of approximately 0.662 MeV). The distance from the source can be fixed or made variable by changing the position of the target or the source. The flux of gamma rays emitted from the source generally decays with the square of the distance from the source and duration of time as governed by the half-life of the isotope.

Without intending to be limited to any particular mechanism, it is believed that the exposure of the nonwoven substrate to ionizing radiation results in free radical sites on the substrate surface which can then subsequently react with the grafting monomers in the imbibing step.

The total dose received by the nonwoven substrate primarily affects the number of radical sites formed on the surface thereof and subsequently the extent to which the grafting monomers are grafted onto the nonwoven substrate.

In some embodiments of the instant method, the irradiated substrate, having free radical sites on the surface of the nonwoven substrate, is imbibed with the monomer solution subsequent to and not concurrent with, the irradiation step. The free radical sites generated on the surface of the nonwoven substrate have average lifetimes ranging from several minutes to several hours and progressively decay to a low concentration within about ten hours at room temperature. Lower temperatures, such as dry ice temperatures, promote longer radical lifetimes. Alternatively, humidification and nitrous oxide can increase the rate of substrate radical formation via generation of hydroxyl radicals.

In some embodiments, the irradiated nonwoven substrate is imbibed with the monomer solution immediately after the irradiation step. Generally when using E-beam the irradiated substrate is imbibed within an hour, preferably within ten minutes. Generally, when using gamma as a source, the substrate should be imbibed immediately after irradiation since irradiation residence time will be long.

In the imbibing step, the nonwoven substrate is contacted with the imbibing solution containing one or more grafting monomers and in amounts previously described. Suitable methods of imbibing include, but are not limited to, spray coating, flood coating, knife coating, Mayer bar coating, dip coating, and gravure coating.

The imbibing solution remains in contact with the nonwoven substrate for a time sufficient for the radical sites to initiate polymerization with the grafting monomers. When imbibed with a solution of monomers, grafting reactions are mostly completed after 12 hours exposure; generally resulting in about 50+ percent conversion of monomers to grafted polymer. As a result, the nonwoven substrate comprises grafted polymers and/or copolymers attached to the interstitial and outer surfaces of the nonwoven substrate.

In some other embodiments of radiation grafting the nonwoven substrate, an embodiment of a "direct radiation grafting" method comprises: 1) providing a nonwoven substrate of the current disclosure; 2) imbibing the nonwoven substrate with a solution comprising one or more grafting monomers having at least one acryloyl group; and 3) exposing the imbibed nonwoven substrate to ionizing radiation, preferably e-beam or gamma radiation, so as to form a functionalized substrate comprising a nonwoven substrate having grafted monomer.

In embodiments of grafting the nonwoven substrate, the grafting monomers have a free-radically polymerizable group. The free-radically polymerizable group is typically an ethylenically unsaturated group such as a (meth)acryloyl group or a vinyl group. The free-radically polymerizable group typically can react with the surface of the nonwoven substrate when exposed to an electron beam or other ionizing radiation. That is, reaction of the free-radically polymerizable groups of the grafting monomers with the surface of the nonwoven substrate in the presence of the electron beam results in the formation of grafted species attached to the nonwoven substrate. One or more grafting monomers may be grafted onto interstitial and outer surfaces of the nonwoven substrate.

In an embodiment of a method that combines "direct radiation grafting" and "UV grafting" techniques comprises: 1) providing a nonwoven substrate of the current disclosure; 2) imbibing the nonwoven substrate with a first solution to form an imbibed nonwoven substrate, the first solution comprising (a) at least one grafting monomer having an acrylate group and a photoinitiator group and (b) one or more monomers having at least one (meth)acryloyl group and at least one additional ethylenically unsaturated, free-radically polymerizable group; and optionally (c) one or more additional monomers having at least one free-radically polymerizable group; 3) exposing the imbibed nonwoven substrate to a controlled amount of electron beam radiation so as to form a first functionalized substrate comprising grafted photoinitiator groups attached to the surfaces of the nonwoven substrate; 4) optionally, imbibing the substrate comprising grafted photoinitiator groups with a second solution comprising one or more additional grafting monomers; and 5) exposing the nonwoven substrate comprising grafted photoinitiator groups to a controlled amount of UV radiation to polymerize or crosslink the remaining ethylenically unsaturated, free-radically polymerizable groups.

As discussed above, the imbibing solution may comprise one or more grafting monomers suitable for grafting onto surfaces of the nonwoven substrate. Any of the exemplary grafting monomers described above can be included in the imbibing solution. In addition to the described grafting monomers, the imbibing solution can contain other materials such as, for example, one or more surfactants, dyes, pigments and solvents.

The concentration of each grafting monomer in the imbibing solution may vary depending on a number of factors including, but not limited to, the grafting monomer or monomers in the imbibing solution, the extent of grafting desired, the reactivity of the grafting monomer(s), and the solvent (if present). Typically, the total concentration of the monomers in the imbibing solution ranges from about 1 weight percent to about 100 weight percent, desirably, from about 5 weight percent to about 30 weight percent, and more desirably from about 15 weight percent to about 25 weight percent based on a total weight of the imbibing solution.

The imbibing solution further comprises an aqueous blend of a water miscible organic solvent and the grafting monomer(s). It has been found that the solvent blend influences the morphology of the grafted polymer and the resulting flux rate when used in separation applications. The ratio of water to organic solvent can vary widely, but is typically greater than 1:1 (v/v) water to organic solvent, preferably greater than 5:1 (v/v), and more preferably greater than 7:1 (v/v). The ratios are generally adjusted so that the resulting grafted nonwoven substrate produces pressure and flux responses suitable for the filtration of an aqueous sample through filter assembly 150.

In some embodiments, the water miscible solvents are protic group containing organic liquids such as the lower alcohols having 1 to 4 carbon atoms, lower glycols having 2 to 6 carbon atoms, and most preferably lower glycol ethers having 3 to 6 carbon atoms and 1 to 2 ether linkages. In some embodiments higher glycols such as poly(ethylene glycol) may be used. Specific examples are methanol, ethanol, n-butanol, t-butyl alcohol, ethylene glycol, methoxyethanol, ethoxyethanol, propoxyethanol, butoxyethanol, methyl carbitol, ethyl carbitol, and mixtures thereof.

In other embodiments, non-protic water miscible organic solvents that can also be used include ketones, amides, and sulfoxides, including, for example, acetone, methyl ethyl ketone, dimethylformamide, dimethylacetamide, N-methylpyrrolidone, and dimethyl sulfoxide.

Once the nonwoven substrate has been imbibed for a desired period of time, the nonwoven substrate bearing grafted polymer groups may be optionally rinsed and/or dried.

In the optional rinsing step, the functionalized nonwoven substrate is washed or rinsed one or more times to remove unreacted monomers, nongrafted oligomers or polymers, solvent or other reaction by-products. Typically, the functionalized substrate is washed or rinsed up to three times using a water rinse, an alcohol rinse, a combination of water and alcohol rinses, and/or a solvent rinse (e.g., acetone, methyl ethyl ketone, etc). When an alcohol rinse is used, the rinse may include one or more alcohols including, but not limited to, isopropanol, methanol, ethanol, or any other alcohol that is practical to use and an effective solvent for any residual monomer. In each rinse step, the functionalized substrate may pass through a rinse bath or a rinse spray. In some embodiments, the rinse may comprise an ionic buffer solution that would reduce swelling of the hydrogel, the amount of retained water, and also avoiding weakening the nonwoven substrate during this rinse step.

In the optional drying step, the functionalized substrate is dried to remove any rinse solution. Typically, the functionalized substrate is dried in oven having a low oven temperature for a desired period of time (referred to herein as "oven dwell time"). Oven temperatures that are "low oven temperatures" typically range from about 60° C. to about 120° C., while oven dwell times typically range from about 2 minutes to about 5 minutes. Any conventional oven may be used in the optional drying step. It should also be noted that in other embodiments the drying step can proceed before the rinsing step to eliminate volatile components before extraction of non-grafted residue. Following the optional drying step, the dried functionalized substrate can be taken up in roll form to be stored for future use.

In yet another method suitable for grafting a hydrogel polymer onto a nonwoven substrate, a UV grafting process may be used wherein the nonwoven substrate is first imbibed with grafting monomers of Formula I, Formula II, or Formula III, including any non-ionic hydrophilic monomers of the current disclosure, followed by UV irradiation, to produce a nonwoven substrate having grafted hydrogel polymer.

In an embodiment of a method of using the microbial detection article of the current description, the method includes: providing the microbial detection article of the current description; providing an aqueous sample; passing the aqueous sample firstly through the microporous membrane and secondly through the water-absorbent layer, wherein the water-absorbent layer retains an aliquot of water from the aqueous sample; incubating the microbial detection article for an incubation period, wherein at least a portion of the aliquot of water contacts the microporous membrane throughout the incubation period; and observing an indication of the presence or absence of microbial growth.

In some embodiments of the method, the incubation period is at least 1 hour, at least 2 hours, at least 4 hours, at least 8 hours, at least at least 12 hours, at least 16 hours, at least 20 hours, or even at least 24 hours.

In some embodiments of the method, the aliquot of water has a volume in a range from 0.5 milliliter to 1.5 milliliter, from 0.8 milliliter to 1.3 milliliter, or even from 0.9 milliliter to 1.1 milliliter.

In some embodiments, the method further comprises: providing a filtration apparatus, the filtration apparatus comprising a filter seat comprising a filter support surface and defining a filter seat inlet and a filter seat outlet; and placing the water-absorbent layer of the microbial detection article against the filter support surface prior to passing the aqueous sample firstly through the microporous membrane and secondly through the water-absorbent layer. In some further embodiments, placing the water-absorbent layer of the microbial detection article against the filter support surface comprises: inserting the filter assembly into the filtration apparatus along an insertion path defined by first and second guide members arranged parallel to each other on opposing sides of the filter seat and lateral to the filter support surface.

Figure 5:
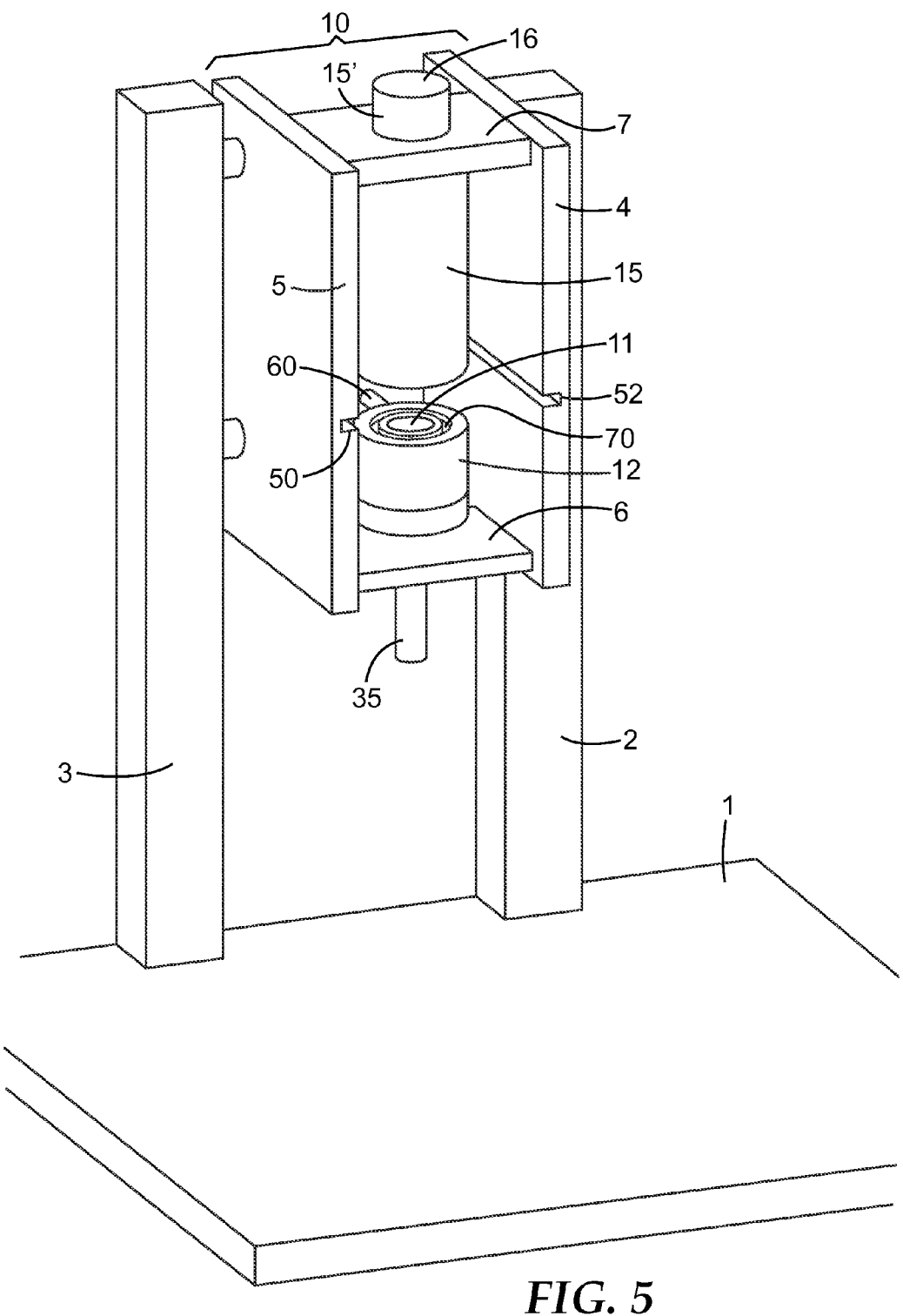
FIG. 5 is a perspective view of a filtration apparatus of the current description.
Figure 6A:
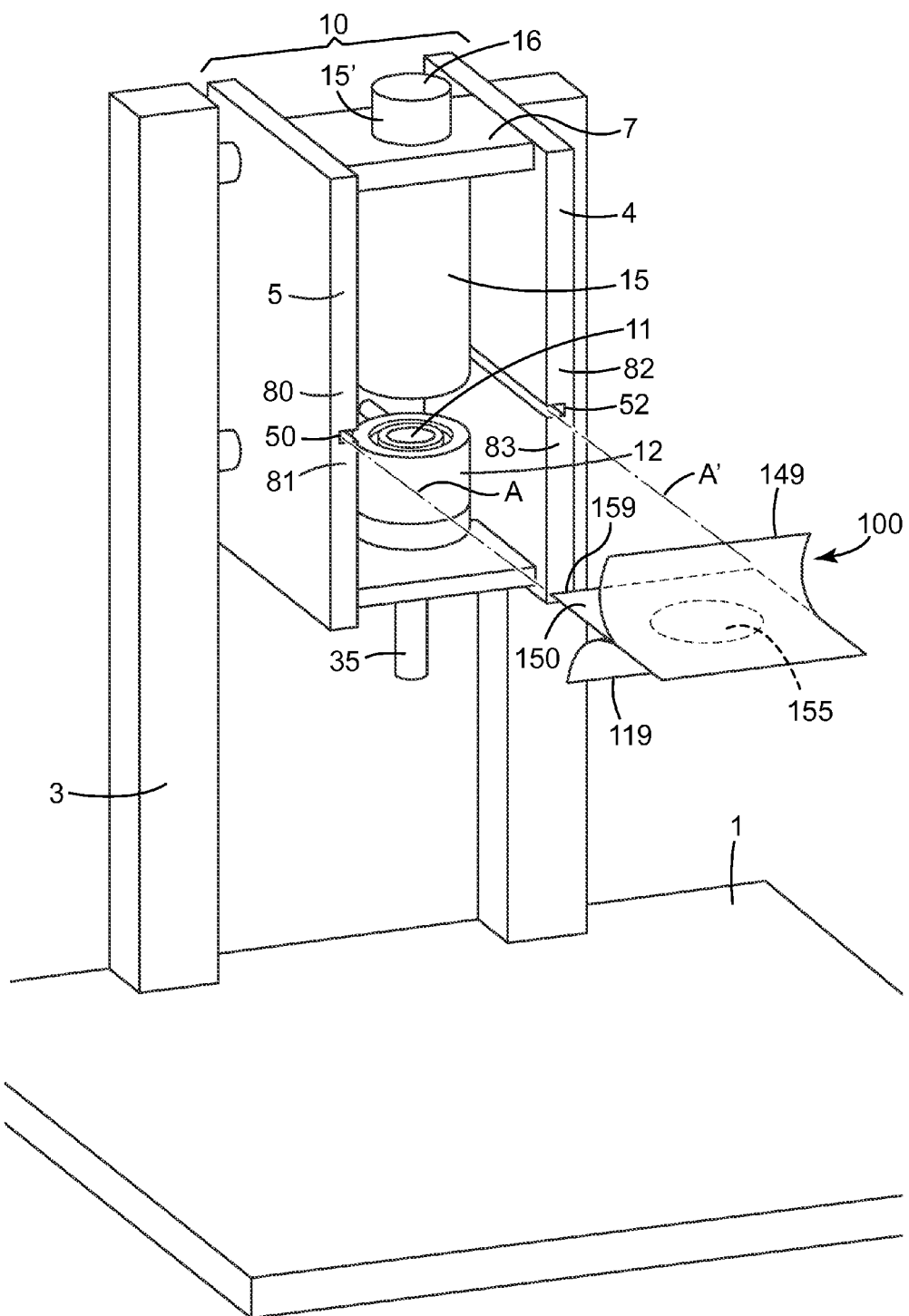
FIGS. 6A and 6B are perspective views of a filtration apparatus of the current description, showing the insertion of an article for detecting microorganisms in an aqueous sample, according to the current description.
Figure 6B:
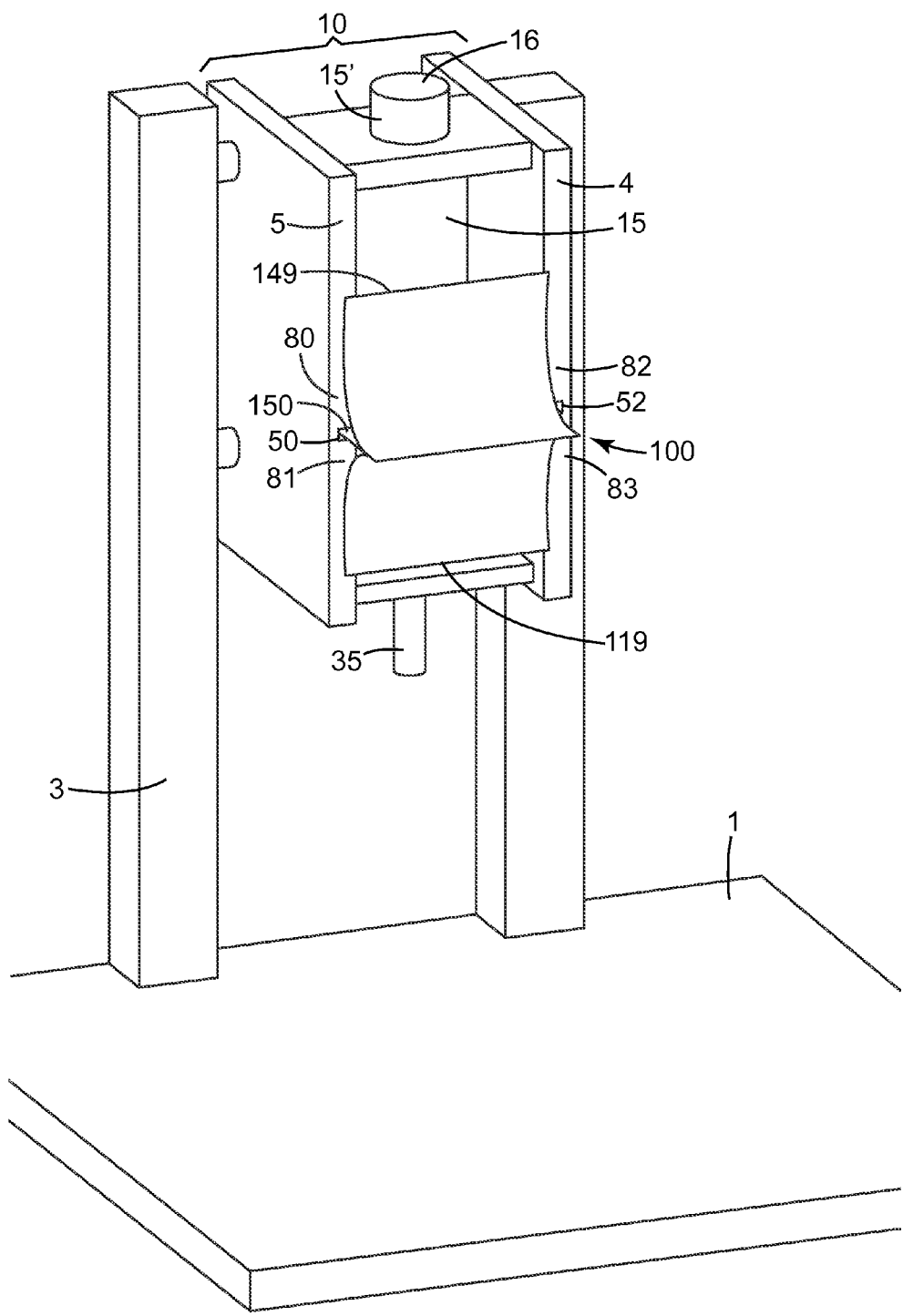

FIGS. 5, 6A, and 6B show an example of a type of filtration apparatus 10 that may be used with the article 100 of the current description. This type of filtration apparatus is described in PCT International Publication No. WO 2012/012172 (Miller et al.), which describes various embodiments of a filtration apparatus useful in the present method. In the embodiment shown, filtration apparatus 10 is mounted upright on posts 2 and 3, which in turn are mounted on base 1; however, filtration apparatus 10 need not be mounted in this fashion, and may be mounted in any suitable manner including, for example, being mounted in a housing that includes front and back walls that have any necessary openings to admit a filter plate device, a sample to be filtered, or a vacuum connection. Filtration apparatus 10 includes a filtration assembly and a guide assembly. The filtration assembly includes a sample head 15 and a filter seat 12 slidably engageable with sample head 15. Sample head 15 is shown as being mounted on a top support plate 7, having a sample head top portion 15' extending above top support plate 7, and defining a sample head inlet 16.

Filter seat 12 rides on a shaft 35 that slides through an opening in bottom support plate 6, permitting filter seat 12 to engage sample head 15. Shaft 35 may be engaged with any suitable handle or mechanism to move filter seat 12 towards or away from sample head 15. Filter seat 12 includes a filter support surface 11, and sample head 15 has a sample head outlet (not shown) that the faces filter support surface 11. In an open position, filter seat 12 and sample head 15 define an insertion gap therebetween.

The guide assembly includes a first guide member 50 and a second guide member 52. First guide member 50 and second guide member 52 are arranged parallel to each other on opposing sides of the filtration assembly to define an insertion path, thereby to guide a filter assembly 150 into the insertion gap. In the filtration apparatus shown in FIG. 5, first guide member 50 and second guide member 52 are notches defined in side walls 4 and 5. Alternatively, other embodiments of first and second guide members may be used, including, for example, slots defined in walls 4 and 5, guide rails mounted on portions of a housing, combinations of these guide members, or any other guide members suitable for guiding a filter plate device into the insertion gap. The first guide member 50 comprises a first end and a second end, and the second guide member 52 comprises a first end and a second end, and the first ends of the first and second guide members are oriented toward the front of filtration apparatus 10 to define an insertion slot arranged to allow a user to insert a filter assembly 150 of article 100 along the insertion slot into filtration apparatus 10.

Filter seat 12 is shown to include a groove 70 suitable for mounting an O-ring (not shown) to aid in sealing the filter seat 12 against a filter membrane layer inserted into the insertion gap. Filter seat 12 also includes a takeoff adapter 60 for connection to a filtrate collection apparatus, which may optionally include a vacuum source.

The article 100 may be used in conjunction with any suitable filtration apparatus, including, for example, a manual clamp-type filtration apparatus that can hold a filter membrane between a sample reservoir and a filtrate collection reservoir, as is commonly used in the filtration of mobile phase liquids for high performance liquid chromatography. A suitable filtration apparatus includes, for example, that clamp-type filtration apparatus available from Sigma-Aldrich (St. Louis, Mo.) under the trade designation "SUPELCO MOBILE PHASE FILTRATION APPARATUS"). It will be understood that a suitable positioning of a clamp on this type of filtration apparatus can hold the composite filter body 155 between the sample reservoir and the filtrate collection reservoir, and that typically this clamp-type filtration apparatus is connected to a vacuum source to aid in passing an aqueous sample from the sample reservoir, through the composite filter body 155, and into the filtrate collection reservoir, while retaining an aliquot of water from the aqueous sample in the water-absorbent layer 180.

In a typical filtering operation, the filter assembly 150 of the article 100 is placed on or into a filtration apparatus to aid with passing an aqueous sample firstly through the microporous membrane and secondly through the water-absorbent layer. Typically, the cover sheet 140 and the base member 110 are both peeled back from the filter assembly 150 during the step of passing an aqueous sample firstly through the microporous membrane and secondly through the water-absorbent layer.

FIG. 6A depicts an embodiment of the article 100 and the filtration apparatus 10 being brought together along a path indicated by A and A' that is aligned with first and second guide members 50 and 52, respectively. The article 100 is shown as having the cover sheet peripheral boundary 149 and the base member peripheral boundary 119 each peeled back from filter assembly 150, which includes the peripheral boundary 159, here shown as aligned with the path indicated by A and A'. FIG. 6A also shows first and second cover sheet support portions 80 and 82, as well as first and second base member support portions 81 and 83. FIG. 6B shows the article 100 having the filter assembly 150 inserted into the filtration apparatus 10, wherein the cover sheet peripheral boundary 149 abuts the first and second cover sheet support portions 80 and 82, and wherein base member peripheral boundary 119 abuts the first and second base member support portions 81 and 83. The first and second cover sheet support portions 80 and 82, and the first and second base member support portions 81 and 83 may each comprise a ramp portion (not shown) to aid in abutting the cover sheet peripheral boundary 149 and the base member peripheral boundary 119 against filtration apparatus 10.

In the configurations depicted in FIGS. 5, 6A, and 6B, the filter seat 12 and the sample head 15 are in the open position, and when the filter assembly 150 is inserted into the filtration apparatus 10, the composite filter body 155 becomes aligned in fluid communication with the filter support surface 11. Typically, filter seat 12 is then urged towards the sample head 15 into a closed position, and contacts the water-absorbent layer 180. An aqueous sample is provided, and the aqueous sample is introduce through sample head 15, then firstly passing through microporous membrane 160 and secondly through water-absorbent layer 180. Optionally, a vacuum source is attached to the takeoff adapter 60 to facilitate flow of the aqueous sample through the composite filter body 155, and into filter seat 12. A typical pressure value for the optional vacuum source is in a range of 30 kiloPascals (kPa) to 50 kPa. Optionally, the aqueous sample may be injected via syringe through a suitable adapter on sample head 15, with sufficient pressure to facilitate flow of the aqueous sample through the composite filter body 155. When the aqueous sample is no longer passing through the microporous membrane 160, the filter seat 12 is typically urged away from the sample head 15 and the article 100 is withdrawn from the filtration apparatus 10. As mentioned above, the water-absorbent layer 180 retains an aliquot of water from the aqueous sample. Typically, the cover sheet 140 and the base member 110 are each then brought into contact with the filter assembly 150. A spreader device may be used to press the cover sheet 140 and the base member 110 against the filter assembly 150 to assure intimate contact of water from the aliquot of water with any optionally included first dry coating 116 (and/or second dry coating 146), thereby wetting the components of those dry coatings, if present.

If the optional vacuum source is employed to facilitate flow of the aqueous sample through the composite filter body 155, the article 100 is typically separated from the optional vacuum source within a short period of time, typically less than 30 seconds, or less than 20 seconds, or less than 10 seconds, or even less than 5 seconds. Separation from the optional vacuum source may include, for example, removing the article 100 from the filtration apparatus, closing a valve between the takeoff adapter 60 and the vacuum source, or switching off the vacuum source. It will be understood that if the vacuum source is allowed to actively draw a vacuum against the composite filter body 155 for a prolonged period (i.e., longer than 60 seconds, although the amount of time may depend upon the level of vacuum pressure) after the aqueous sample has passed through the microporous membrane 160, the water activity ($A_W$) value of the composite filter body 155 may diminish.

After the above filtration operation, the article 100, including the aliquot of water from the aqueous sample and any microorganisms that may have been captured on the microporous membrane 160, is incubated for an incubation period, in order to permit growth of microorganisms (if present).

It will be understood that the incorporation of the water-absorbent layer 180 into the microbial detection article 100 greatly simplifies the operation of processing an aqueous sample for the detection of microorganisms therein, with no additional hydration of media needed. Additionally, there is a reduced potential for inadvertent contamination during hydration of the microbial detection article, as compared with, for example, the need to hydrate other culture devices with water from an additional source.

The method further comprises incubating the article 100 for an incubation period, wherein at least a portion of the aliquot of water contacts the microporous membrane throughout the incubation period. The incubation provides the conditions (i.e., time, temperature) to facilitate the growth of a microorganism, if present. A person of ordinary skill in the relevant art will recognize that the incubation temperature may be selected according to the microorganism to be detected. For example, if a yeast or mold is to be detected, the first incubation temperature typically may be from about 23° C. to about 32° C. For example, if a bacterium is to be detected, the incubation temperature typically may be from about room temperature to about 45° C.

According to the present disclosure, the incubation period may be as short as one hour. In some embodiments, the first incubation is less than 2 hours, less than 3 hours, less than 4 hours, less than 5 hours, less than 6 hours, less than 7 hours, less than 8 hours, less than 9 hours, less than 10 hours, less than 11 hours, less than 12 hours, less than 13 hours, less than 14 hours, less than 15 hours, less than 16 hours, less than 24 hours, less than 36 hours, or even less than 48 hours.

Contact between the hydrated region of the microporous membrane and the second dry coating permits hydration of the second dry coating 146 and, thereby, an interaction of a detection reagent, a lysis agent, or a selective agent in the second dry coating 146 with a microorganism (if present), a component of the microorganism, and/or a metabolic byproduct of the microorganism. The interaction can provide a detectable signal.

The method further comprises observing an indication of the presence or absence of microbial growth. The indication may be observable visually and/or by an instrument (e.g., an imaging system) and both types (manual and automated) of detection are contemplated by the present disclosure.

The nature of the indication of microbial growth generally is dependent upon the detection reagent (or plurality of detection reagents) in the article 100. For example, certain detection reagents (e.g., enzyme substrates) produce a detectable colored or fluorescent product when they interact with a microbe or a component thereof. For example, certain detection reagents (e.g., pH indicators) produce a detectable change in color or fluorescence in the presence of acidic or basic metabolic products of microorganisms. For example, certain detection reagents (e.g., polysaccharide or polypeptide polymers) are relatively opaque in their native state and become relatively transparent when degraded by microorganisms or components thereof.

In some embodiments, an indication of the presence of microbial growth comprises the presence of a detectable microbial colony. The microbial colony may be detected visually. The microbial colony may be detected using an imaging system. Suitable systems for detecting microbial colonies are described, for example, in International Patent Publication No. WO 2005/024047 (Graessle et al.); U.S. Patent Application Publication Nos. 2004/0101954 (Graessle et al.) and 2004/0102903 (Graessle et al.); and U.S. Patent Application Ser. No. 61/187,107, filed Jun. 15, 2009. Suitable imaging systems include, for example, that plate reader available from 3M Company (St. Paul, Minn.) under the trade designation "PETRIFILM PLATE READER", that colony counter available from Spiral Biotech (Norwood, Mass.) under the trade designation "PETRISCAN", and those plate scanners available from Synbiosis (Cambridge, U.K.) under the trade designations "PROTOCOL" and "ACOLYTE".

In some embodiments, an indication of the presence of microbial growth comprises the presence of a reaction, detected visually or by instrument, associated with a non-visually-detectable microbial colony.

In any one of the above embodiments, the method can further comprise enumerating microorganisms. In some embodiments, the microorganisms can be enumerated by counting the number of discrete colonies in the article. In some embodiments, the microorganisms can be enumerated by counting the number of discrete reactions (e.g., colored zones, fluorescent zones, clear zones) that are associated with non-visually-detectable colonies in the article. Enumerating microorganisms may comprise using an imaging system to enumerate microorganisms.

Observing an indication of the presence or absence of microbial growth may comprise obtaining an image of the article. Observing an indication of the presence or absence of microbial growth may further comprise printing, displaying, or analyzing the image.

Embodiments of the current disclosure include:
1. A microbial detection article comprising:
   a base member comprising a self-supporting water impervious substrate with first and second generally opposed major surfaces;
   a filter assembly defining a filter assembly aperture therein, and having a composite filter body mounted across the filter assembly aperture; wherein the composite filter body comprises:
   a microporous membrane, and
   a water-absorbent layer in fluid communication with the microporous membrane; and
   a cover sheet;
wherein the filter assembly is positioned between the cover sheet and the base member, and wherein the water-absorbent layer is positioned between the microporous membrane and the base member.

2. The article of item 1, further comprising a spacer layer defining a spacer aperture therein, wherein the spacer layer is mounted on a major face of the filter assembly facing the first major surface of the base number, and wherein the spacer aperture is in fluid communication with the filter assembly aperture.

3. The article of any preceding item, wherein the filter assembly is attached to the base member, and wherein the cover sheet is attached to the base member.

4. The article of any preceding item, wherein the cover sheet comprises a water-soluble gelling agent.

5. The article of item 4, wherein the cover sheet comprises a nutrient medium.

6. The article of item 4, wherein the cover sheet comprises a detection reagent.

7. The article of any preceding item, wherein the microporous membrane comprises a material selected from the group consisting of polyethersulfone, nylon, polycarbonate, polyester, cellulose acetate, mixed cellulose esters, polyvinylidene fluoride, nitrocellulose, a ceramic, a derivative of any of the foregoing, and any combination of these.

8. The article of any preceding item, wherein the water-absorbent layer comprises a nonwoven substrate having:
   an average fiber size in a range from 0.7 micrometer to 15 micrometers;
   a void volume in a range from 50% to 95%; and
   a hydrogel polymer comprising grafting monomer units grafted to the surface of the nonwoven substrate, wherein the grafting monomer units are selected from the group consisting of ionic grafting monomer units, non-ionic hydrophilic grafting monomer units, and mixtures thereof.

9. The article of item 8, wherein the average fiber size is in a range from 1 micrometer to 6 micrometers.

10. The article of item 8, wherein the ionic grafting monomer units comprise cationic monomer units.

11. The article of item 8, wherein the ionic grafting monomer units comprise anionic monomer units.

12. The article of item 8, wherein the non-ionic hydrophilic monomer units are selected from the group consisting of dimethylacrylamide and 2-hydroxyethyl(meth)acrylate.

13. The article of any preceding item, wherein the nonwoven substrate has a surface area in a range from 15 square meters per square meter of nonwoven substrate to 50 square meters per square meter of nonwoven substrate.

14. The article of any preceding item, wherein the nonwoven substrate has a mean pore size in a range from 1 micrometer to 40 micrometers according to the Porosity Test.

15. The article of item 8, wherein a weight of the hydrogel polymer comprising the monomer units grafted to the surface of the nonwoven substrate is in a range from 0.5 to 5 times a weight of the nonwoven substrate.

16. The article of any preceding item, wherein the water-absorbent nonwoven substrate is a hydrophilic thermoplastic polymer substrate.

17. The article of any preceding item, wherein water-absorbent nonwoven substrate is a polyamide nonwoven substrate.

18. The article of any preceding item, wherein the water-absorbent nonwoven substrate is a nylon nonwoven substrate having an average effective fiber diameter of not greater than 1 micrometer.

19. The article of any preceding item, wherein the water-absorbent layer has a Water Absorption Capacity Ratio in a range of from 0.5 to 30, according to the Water Absorption Capacity Test Method.

20. The article of any preceding item, wherein the water-absorbent layer has a Water Absorption Capacity Ratio in a range of from 1 to 10, according to the Water Absorption Capacity Test Method.

21. The article of any preceding item, wherein the water-absorbent layer has a Water Absorption Capacity Ratio in a range of from 2 to 5, according to the Water Absorption Capacity Test Method.

22. A method of testing for the presence of a microorganism in an aqueous sample, the method comprising:
 providing the microbial detection article of any one of items 1 to 21;
 providing an aqueous sample;
 passing the aqueous sample firstly through the microporous membrane and secondly through the water-absorbent layer, wherein the water absorbent layer retains an aliquot of water from the aqueous sample;
 incubating the microbial detection article for an incubation period, wherein at least a portion of the aliquot of water contacts the microporous membrane throughout the incubation period; and
 observing an indication of the presence or absence of microbial growth.

23. The method of item 22, wherein the incubation period is at least 8 hours.

24. The method of item 22, wherein the incubation period is at least 12 hours.

25. The method of item 22, wherein the incubation period is at least 24 hours.

26. The method of item 22, wherein the aliquot of water has a volume in a range from 0.5 milliliters to 1.5 milliliters.

27. The method of item 22, further comprising contacting the microporous membrane with the cover sheet, wherein the cover sheet comprises a nutrient and a detection reagent.

28. The method of item 22, further comprising:
 providing a filtration apparatus, the filtration apparatus comprising a filter seat comprising a filter support surface and defining a filter seat inlet and a filter seat outlet; and
 placing the water-absorbent layer of the microbial detection article against the filter support surface prior to passing the aqueous sample firstly through the microporous membrane and secondly through the water-absorbent layer.

29. The method of item 28, wherein placing the water-absorbent layer of the microbial detection article against the filter support surface comprises:
 inserting the filter assembly into the filtration apparatus along an insertion path defined by first and second guide members arranged parallel to each other on opposing sides of the filter seat and lateral to the filter support surface.

The invention will be further illustrated by reference to the following non-limiting Examples. All parts and percentages are expressed as parts by weight unless otherwise indicated.

EXAMPLES

Porosity Test Method

Mean flow pore size was measured according to ASTM F316-03 Standard Test Methods for Pore Size Characteristics of Membrane Filters by Bubble Point and Mean Flow Pore Test Method B using a test fluid available from DuPont (Wilmington, Del.) under the trade designation "FREON TF".

Water-Absorption Capacity Test Method

A 50 milliliter sample of phosphate-buffered saline was drawn through a 47 millimeter diameter composite filter body including a microporous membrane and a water-absorbent layer (see, for example, Preparative Example C below), using vacuum filtration with vacuum pressure of 85 kilopascal during the flow of water through the composite filter body. Weights of the composite filter body before and after filtration were obtained, and a Water-Absorption Capacity Ratio was calculated, using a weight of water retained in the composite filter body compared to a weight of the water absorbent layer (calculated as a weight of the composite filter body minus a typical mass of components other than the water-absorbent layer):

$$C_{WA}=[(A-B)/(B-K)]$$

where:
$C_{WA}$=Water Absorption Capacity Ratio
A=final mass of composite filter body and water
B=initial mass of composite filter body, and
K=typical mass of composite filter body components, excluding water-absorbent layer In a variant of the Water-Absorption Capacity Test Method, called the "Water-Absorbent Layer Capacity Test Method", the weight of the water absorbent layer alone is measured prior to incorporation of the water-absorbent layer into the composite filter body, and the Water-Absorption Capacity ratio ($C_{wA}$) is calculated using the measured weight of the water-absorbent layer:

$$C_{WA}=[(A-B)/D]$$

where:

$C_{WA}$=Water Absorption Capacity Ratio

A=final mass of composite filter body and water

B=initial mass of composite filter body, and

D=initial mass of water-absorbent layer, prior to incorporation in composite filter body Preparative Example A Nylon Nonwoven Substrate Using the method described in paragraph [0146] of U.S. Published Pat. App. No. 2010/0155323 (Weiss et al.), published Jun. 24, 2010, a nylon nonwoven substrate was prepared wherein a nylon-6 available from BASF Corporation Engineering Plastics (Wyandotte, Mich.) under the trade designation "B-3" was used to produce meltblown nonwoven substrate. The melt temperature was 265° C. with a mass flow rate of 0.25 gram/hole/minute on a standard meltblowing drilled orifice die. Hot air at 1000 SCFM (28 CMM per meter of die width) at a temperature of 350° C. was used to attenuate the fibers. The fibers were collected 0.43 meter away from the die on a foraminous stainless steel belt and were bonded under 200° C. air drawn through the web at 137 (meters per minute) face velocity for 0.14 second followed by cooling air at 29° C. at the same face velocity for 0.8 second. The collected web was 50 grams per square meter and had an effective fiber diameter of 5.8 micrometers. The collected web had a thickness of 0.81 mm before calendaring between two 25 centimeter diameter smooth steel rolls set at 82° C. running at 1.5 meter/minute with a nip pressure of 176 Newtons per lineal centimeter (N/lcm) of web. The resulting web thickness was 0.25 millimeter.

Preparative Example B

Water-Absorbent Nylon Nonwoven Layer

Using the method described in paragraphs [0153]-[0155] of U.S. Published Pat. App. No. 2010/0155323 (Weiss et al.), published Jun. 24, 2010, a 30 centimeter by 43 centimeter sample of the nylon nonwoven substrate of Preparative Example A was purged of air under a nitrogen atmosphere in a glove box and inserted into a "ZIPLOC" plastic bag and sealed. The sealed bag was then removed from the glove box and irradiated to a dose level of 40 kGy by passing it through the electron beam set with an accelerating voltage of 300 kV and a web speed of 20 feet/minute. After returning the sealed bag to the nitrogen atmosphere-controlled glove box, the irradiated nonwoven substrate was removed and placed inside a non-irradiated, nitrogen purged, "ZIPLOC" bag.

The freshly prepared nonwoven sample was imbibed with 100 grams of the nitrogen purged imbibing solution comprising 15 weight percent 3-[(methacryloylamino)propyl]trimethylammonium chloride (MAPTAC) monomer, 15 weight percent methanol, 10 weight percent polyethylene glycol with hydroxy end groups, average molecular weight 4,000 g/mole (PEG 4000) and 60 weight percent water, and the bag resealed after expelling most of the nitrogen. During this step the oxygen level within the glove box was generally maintained below 40 parts per million (ppm).

The sample was maintained flat in the bag and evenly saturated for four hours by occasionally rotating the bag. The resulting grafted nylon nonwoven substrate was removed from the bag and carefully washed by soaking it for 10 minutes in a tray containing 2 liters of fresh deionized water. The substrate was removed from the tray, compressed between multiple layers of paper towels and the washing process repeated two more times with fresh DI water and air dried, to provide the water-absorbent nylon nonwoven layer.

Preparative Example C

Composite Filter Body and Demonstration of Water-Absorption

A 47 millimeter polycarbonate microporous membrane obtained from Whatman Inc. (Florham Park, N.J.) under the trade designation "WHATMAN POLYCARBONATE MEMBRANE FILTER NO. 111107" was laid on top of a similar size piece of the water-absorbent nylon nonwoven layer of Preparative Example B above to form a composite filter membrane, and the periphery of this composite filter membrane was sealed with an annular gasket die-cut from biaxially oriented polypropylene (BOPP, 1.6 mil (0.04 mm) thickness) film coated with a thin layer of pressure sensitive adhesive (96 weight percent iso-octyl acrylate and 4 weight percent acrylic acid), to complete formation of a composite filter body. The ability of the composite filter membrane to retain water was determined by weighing the dry composite filter membrane (dry weight=323 milligrams), then filtering 50 milliliters of phosphate-buffered saline with the aid of a vacuum filtration apparatus, and then weighing the wet composite filter membrane (wet weight=1530 milligrams; water weight=1530 milligrams-323 milligrams=1207 milligrams).

Preparative Example D

Filter Assembly

An annular gasket was die-cut from biaxially-oriented polypropylene (BOPP, 1.6 mil (0.04 millimeter) thickness) film coated with a thin layer of pressure sensitive adhesive (96 weight percent iso-octyl acrylate and 4 weight percent acrylic acid). The outer diameter of the gasket was 52 millimeters and the inner diameter of the gasket was 45 millimeters.

A circular hole (44 millimeters in diameter) was die cut from a rectangular sheet (75 millimeters by 95 millimeters) of BOPP (1.6 mil (0.04 millimeter) thickness). A nylon membrane filter (47 millimeters, 0.45 millimeter nominal pore size, obtained from Alltech Associates (Deerfield, Ill.)) was centered over the hole on the adhesive-coated side of the BOPP sheet. The adhesive side of the gasket was centered over the outer edge of the membrane filter and was pressed against the filter and the BOPP sheet, sealing the edge of the membrane filter to the BOPP sheet. Next, another adhesive gasket (of the same dimensions) was die-cut to attach a water-absorbent nylon nonwoven layer of Preparative Example C, of equal diameter to the membrane, to the opposite side of the BOPP film.

Example 1

Detection Article

A ⅞ inch (22 millimeter) diameter circular hole was die-cut into a 3 inch×4 inch piece of biaxially-oriented polypropylene (BOPP, 1.6 mil (0.04 millimeter) thickness) film (obtained from Vifan Inc, Morristown, Tenn.). A larger 50 millimeter circular hole was die-cut into a 3 inch×4 inch piece of foam dam (0.56 millimeter thickness) and the foam dam was then adhered to the previously die-cut BOPP film using the adhesive present on the foam dam. Next, adhesive gaskets were die-cut out of adhesive coated BOPP to have an outside diameter of approximately 1 3/16 inches (30 millimeters) and an inside diameter of approximately 3/4 inch (19 millimeters) and were used to attach a 25 millimeter diameter 0.45 micrometer pore size membrane obtained from Whatman Inc. (Florham Park, N.J.) under the trade designation "WHATMAN POLYCARBONATE MEMBRANE FILTER NO. 111107" to the opposite side of the BOPP film, overlaying the die-cut hole. Next, another adhesive gasket (of the same dimensions) was die-cut to attach a water-absorbent nylon nonwoven layer of Preparative Example C, of equal diameter to the membrane, to the opposite side of the BOPP film, to complete formation of a filter assembly.

The filter assembly so prepared was inserted between the cover sheet and base member of an aerobic count plate obtained from 3M Company (St. Paul. MN) under the trade designation "AC PETRIFILM", where the cover sheet had been removed and powder coated with Standard Methods Nutrients. The powder coating was performed by placing the cover sheet into a plastic bag containing 5 grams of Standard Methods Nutrients and shaking the bag for 30 seconds. The filter assembly was attached to the base member of the "AC PETRIFILM" using double-sided hinge tape along an edge, and the powder coated cover sheet was then similarly attached to the exposed side of the filtration sheet along the same edge.

It will be apparent to those skilled in the art that the specific exemplary structures, features, details, configurations, etc. that are disclosed herein can be modified and/or combined in numerous embodiments. All such variations and combinations are contemplated by the inventor as being within the bounds of the conceived invention. Thus, the scope of the present invention should not be limited to the specific illustrative structures described herein, but rather extends at least to the structures described by the language of the claims, and the equivalents of those structures. To the extent that there is a conflict or discrepancy between this specification and the disclosure in any document incorporated by reference herein, this specification will control.

What is claimed is:

1. A microbial detection article comprising:
    a base member comprising a self-supporting water impervious substrate with a first major surface and a second major surface that is generally opposed to the first major surface;
    a filter assembly defining a filter assembly aperture therein, and having a composite filter body mounted across the filter assembly aperture; wherein the composite filter body comprises:
        1) a filter support layer having the filter assembly aperture,
        2) a microporous membrane positioned on a first side of the filter support, wherein the microporous membrane overlays the filter assembly aperture and extends beyond the perimeter of the filter assembly aperture, and
        3) a water-absorbent layer positioned on a second side of the filter support opposite the microporous membrane, wherein the water absorbent layer is positioned under the filter assembly aperture, is in fluid communication with the microporous membrane, and extends beyond the perimeter of the filter assembly aperture, wherein the water absorbent layer comprises a fibrous substrate functionalized with a grafted hydrogel polymer; and
    a cover sheet;
    wherein
        the filter assembly is positioned between the cover sheet and the base member;
        the filter assembly is coupled to the cover sheet, to the base member, or to both; and the water-absorbent layer is positioned between the microporous membrane and the base member.

2. The article of claim 1, further comprising a spacer layer defining a spacer aperture therein, wherein the spacer layer faces the first major surface of the substrate, and wherein the spacer aperture is in fluid communication with the filter assembly aperture.

3. The article of claim 1, wherein the filter assembly is attached to the base member, and wherein the cover sheet is attached to the base member.

4. The article of claim 1, wherein the cover sheet further comprises at least one of a water-soluble gelling agent, a nutrient medium, or a detection reagent.

5. The article of claim 1, wherein the microporous membrane comprises a material selected from the group consisting of polyethersulfone, nylon, polycarbonate, polyester, cellulose acetate, mixed cellulose esters, polyvinylidene fluoride, nitrocellulose, a ceramic, a derivative of any of the foregoing, and any combination of these.

6. The article of claim 1, wherein the water-absorbent layer comprises a nonwoven substrate having:
    an average fiber size in a range from 0.7 micrometer to 15 micrometers;
    a void volume in a range from 50% to 95%; and
    a hydrogel polymer comprising grafting monomer units grafted to a surface of the nonwoven substrate, wherein the grafting monomer units are selected from the group consisting of ionic grafting monomer units, non-ionic hydrophilic grafting monomer units, and mixtures thereof.

7. The article of claim 6, wherein the ionic grafting monomer units comprise cationic monomer units.

8. The article of claim 6, wherein the ionic grafting monomer units comprise anionic monomer units.

9. The article of claim 6, wherein the non-ionic hydrophilic monomer units are selected from the group consisting of dimethylacrylamide and 2-hydroxyethyl(meth)acrylate.

10. The article of claim 6, wherein the nonwoven substrate has a surface area in a range from 15 square meters per square meter of nonwoven substrate to 50 square meters per square meter of nonwoven substrate.

11. The article of claim 6, wherein the nonwoven substrate has a mean pore size in a range from 1 micrometer to 40 micrometers.

12. The article of claim 6, wherein a weight of the hydrogel polymer comprising the monomer units grafted to the surface of the nonwoven substrate is in a range from 0.5 to 5 times a weight of the nonwoven substrate.

13. The article of claim 6, wherein the nonwoven substrate is a hydrophilic thermoplastic polymer substrate.

14. The article of claim 6, wherein nonwoven substrate is a polyamide nonwoven substrate.

15. The article of claim 6, wherein the nonwoven substrate is a nylon nonwoven substrate having an average effective fiber diameter of not greater than 1 micrometer.

16. The article of claim 6, wherein the water-absorbent layer has a Water Absorption Capacity Ratio in a range of from 0.5 to 30.

17. A method of testing for the presence of a microorganism in an aqueous sample, the method comprising:
    providing the microbial detection article of claim 1;
    providing an aqueous sample;
    passing the aqueous sample firstly through the microporous membrane and secondly through the water-absorbent layer, wherein the water absorbent layer retains an aliquot of water from the aqueous sample;

incubating the microbial detection article for an incubation period, wherein at least a portion of the aliquot of water contacts the microporous membrane throughout the incubation period; and observing an indication of the presence or absence of microbial growth.

18. The method of claim 17, wherein the incubation period is less than 24 hours.

19. The method of claim 17, further comprising:

providing a filtration apparatus, the filtration apparatus comprising a filter seat comprising a filter support surface and defining a filter seat inlet and a filter seat outlet; and placing the water-absorbent layer of the filter plate article against the filter support surface prior to passing the aqueous sample firstly through the microporous membrane and secondly through the water-absorbent layer.

20. A filtration apparatus for use with a microbial detection article of claim 1, the filtration apparatus comprising:

(a) a filtration assembly comprising:
   (i) a filter seat comprising a filter support surface and defining a filter seat inlet, a filter seat outlet; and
   (ii) a sample head defining a sample head inlet and a sample head outlet;
wherein the filter seat is slidably engageable with the sample head to define an insertion gap between the filter support surface and the sample head outlet; and (b) a guide assembly comprising a first guide member and a second guide member, wherein the first guide member and the second guide member are arranged parallel to each other on opposing sides of the filtration assembly to define an insertion path, thereby to guide the filter membrane layer of the filter article into the insertion gap.

* * * * *

UNITED STATES PATENT AND TRADEMARK OFFICE
CERTIFICATE OF CORRECTION

PATENT NO. : 8,906,645 B2
APPLICATION NO. : 13/809214
DATED : December 9, 2014
INVENTOR(S) : Steven Swanson et al.

It is certified that error appears in the above-identified patent and that said Letters Patent is hereby corrected as shown below:

In The Specification

Column 1
Line 28, delete "enteriditis," and insert -- enteritidis, --, therefor.

Line 64, delete "water absorbent" and insert -- water-absorbent --, therefor.

Column 4
Lines 15-16, delete "parahemolyticus," and insert -- parahaemolyticus, --, therefor.

Line 16, delete "cholerasuis," and insert -- choleraesuis, --, therefor.

Column 7
Line 63, delete "bromthymol" and insert -- bromothymol --, therefor.

Line 63, delete "bromcresol" and insert -- bromocresol --, therefor.

Line 63, delete "anthroquinone" and insert -- anthraquinone --, therefor.

Column 8
Line 52, delete "phophatases" and insert -- phosphatases --, therefor.

Column 9
Line 26, delete "Am." and insert -- Am --, therefor.

Line 37, delete "anthroquinone" and insert -- anthraquinone --, therefor.

Column 20
Line 3, delete "polypropylene" and insert -- poly(propylene --, therefor.

Signed and Sealed this
Fourteenth Day of July, 2015

Michelle K. Lee
*Director of the United States Patent and Trademark Office*

CERTIFICATE OF CORRECTION (continued)
U.S. Pat. No. 8,906,645 B2

Column 29
Line 63, delete "61/187,107," and insert -- 61/187,107, (Attorney Docket No. 65250US002) --, therefor.

Column 30
Line 2, delete "Synbiosis" and insert -- Symbiosis --, therefor.

Column 31
Line 53, delete "water absorbent" and insert -- water-absorbent --, therefor.

Column 32
Line 48, delete "water absorbent" and insert -- water-absorbent --, therefor.

Line 62, delete "water absorbent" and insert -- water-absorbent --, therefor.

In The Claims

Column 35
Line 57, in Claim 1, delete "water absorbent" and insert -- water-absorbent --, therefor.

Line 61, in Claim 1, delete "water absorbent" and insert -- water-absorbent --, therefor.

Column 37
Line 1, in Claim 17, delete "water absorbent" and insert -- water-absorbent --, therefor.